United States Patent
Goldenberg et al.

(10) Patent No.: US 8,420,786 B2
(45) Date of Patent: Apr. 16, 2013

(54) BISPECIFIC ANTIBODY TARGETING A COMPLEMENT FACTOR OR COMPLEMENT REGULATORY PROTEIN

(75) Inventors: David M. Goldenberg, Mendham, NJ (US); Hans J. Hansen, Picayune, MS (US)

(73) Assignee: Immunomedics, Inc., Morris Plains, NJ (US)

( * ) Notice: Subject to any disclaimer, the term of this patent is extended or adjusted under 35 U.S.C. 154(b) by 959 days.

(21) Appl. No.: 11/929,279

(22) Filed: Oct. 30, 2007

(65) Prior Publication Data

US 2008/0241145 A1 Oct. 2, 2008

Related U.S. Application Data

(62) Division of application No. 11/296,432, filed on Dec. 8, 2005.

(60) Provisional application No. 60/634,076, filed on Dec. 8, 2004.

(51) Int. Cl.
C07K 16/00 (2006.01)
(52) U.S. Cl.
USPC ............................................. 530/387.3
(58) Field of Classification Search .................. None
See application file for complete search history.

(56) References Cited

U.S. PATENT DOCUMENTS

| | | | |
|---|---|---|---|
| 6,132,992 | A | 10/2000 | Ledbetter et al. |
| 6,572,856 | B1 * | 6/2003 | Taylor et al. ............... 424/130.1 |
| 2002/0192217 | A1 * | 12/2002 | Calandra et al. ........... 424/145.1 |
| 2004/0137001 | A1 * | 7/2004 | Schreiber et al. .......... 424/170.1 |
| 2004/0228860 | A1 * | 11/2004 | Taylor et al. ............... 424/144.1 |
| 2004/0242851 | A1 * | 12/2004 | Zhu ........................ 530/388.22 |
| 2005/0049402 | A1 * | 3/2005 | Babcook et al. ........ 530/388.23 |
| 2005/0152903 | A1 * | 7/2005 | Newman et al. .......... 424/145.1 |
| 2005/0202010 | A1 * | 9/2005 | Giroir et al. .............. 424/144.1 |
| 2005/0221284 | A1 * | 10/2005 | Taylor et al. .................. 435/5 |
| 2006/0166284 | A1 * | 7/2006 | Light et al. .................. 435/7.5 |
| 2007/0274989 | A1 * | 11/2007 | Fung et al. ................. 424/136.1 |
| 2008/0241141 | A1 * | 10/2008 | Goldenberg et al. ...... 424/136.1 |
| 2008/0241145 | A1 * | 10/2008 | Goldenberg et al. ...... 424/138.1 |

OTHER PUBLICATIONS

Levy et al., Crit. Care. Med, 2003, 31: 1250-1256.*
Medline Plus, accessed Sep. 8, 2011, 3 pages.*
Furuta et al., J. Am. Chem. Soc. 2011, 133: 5788-5790.*
Zioncheck et al., J. Biol. Chem. 1992, 267: 3561-3564.*
Ostuni et al., Cell. Mol. Life Sci. 2010, 67: 4109-4134.*
Lohela et al., Current Opinion in Cell Biology 2009, 21: 154-165.*
Grotzinger, Biochim. Biophys. Acta 2002, 1592: 215-223.*
Kuhn et al., J. Immunol. 1998, 160: 5088-5097.*
Davis et al., Immunobiology 2007, 212: 313-323.*
Sequence alignment, 2011, 3 pages.*
Gupta et al., Blood, prepublished online Jan. 23, 2012; doi:10.1182/blood~2011~09~381988 (reference provided by Applicant).*
Sahu, Arvind et al.; "Complement inhibitors: a resurgent concept in anti-inflammatory therapeutics"; accepted Mar. 28, 2000 Immunopharmacology; pp. 133-138.; 0162-3109/00; Elsevier Science B.V., Philadelphia, P.A. USA.
Houston, Donald; "Tissue factor-a therapeutic target for thrombotic disorders"; Expert Opinion Ther. Targets 2002; pp. 159-174; 1472-8222; Ashley Publications ISSN; Winnipeg, Manitoba Canada.
International Search Report issued in PCT/US05/44446, mailed Jun. 16, 2006.

* cited by examiner

*Primary Examiner* — Ilia Ouspenski
(74) *Attorney, Agent, or Firm* — Rossi, Kimms & McDowell LLP

(57) ABSTRACT

A multispecific antagonist is disclosed that reacts specifically with at least two different targets. The targets are (A) proinflammatory effectors of the innate immune system, (B) coagulation factors, (C) complement factors and complement regulatory proteins, and (D) targets specifically associated with an inflammatory or immune-dysregulatory disorder or with a pathologic angiogenesis or cancer, wherein this latter target is not (A), (B) or (C). At least one of the targets is (C), and when the multispecific antagonist comprises a single multispecific antibody, then CD74 is excluded as a target of said antagonist. When the multispecific antagonist comprises a combination of separate antibodies, combinations are excluded where one of said antibodies targets a B-cell antigen and the other antibody targets a T-cell, plasma cell, macrophage or inflammatory cytokine and combinations are also excluded where one of said antibodies targets CD20 and the other antibody targets C3b or CD40.

13 Claims, No Drawings

BISPECIFIC ANTIBODY TARGETING A COMPLEMENT FACTOR OR COMPLEMENT REGULATORY PROTEIN

This application is a divisional of U.S. Ser. No. 11/296,432, filed on Dec. 8, 2005, which claims the benefit of U.S. Provisional Application No. 60/634,076, filed on Dec. 8, 2004.

BACKGROUND OF THE INVENTION

A. Field of the Invention

The invention relates generally to methods and compositions for immunotherapy of inflammatory and immune-dysregulatory diseases, using multispecific antagonists that target at least two different markers. The markers are antigens and/or receptors on lymphocytes, macrophages, monocytes, or dendritic cells (DCs). The invention particularly relates to methods and compositions for modulating receptors on immune-targeting and immune-processing cells using specific antibodies and antibody heteroconjugates to bind to the cells and their receptors, to effect a treatment of various diseases that are generated or exacerbated by, or otherwise involve, these cells and their receptors. Such diseases more particularly include acute and chronic inflammatory disorders, autoimmune diseases, septicemia and septic shock, neuropathies, graft versus host disease, acute respiratory distress syndrome, granulomatous diseases, giant cell arteritis, acne, diffuse intravascular coagulation (DIC), transplant rejection, asthma, cachexia, myocardial ischemia, and atherosclerosis. The methods and compositions also are useful in treating pathological angiogenesis and cancer. The methods and compositions can include a secondary therapeutic that is directed to a cancer receptor or cancer-associated antigen. Methods and compositions are also described for improved diagnosis/detection of the diseases.

B. Description of the Related Art

The immune system comprises both the innate immune system and the adaptive, or acquired immune system. Many host cells participate in the processes of innate and adaptive immunity, such as neutrophils, T- and B-lymphocytes, macrophages and monocytes, dendritic cells, and plasma cells. They usually act in concert, affecting one another, particularly in the regulation of certain factors and cytokines that contribute to the recognition and processing of innate and external noxients, and these systems have evolved over the millions of years of the development of vertebrate, mammalian, and human organisms.

A major goal of immunotherapy is to exploit or enhance a patient's immune system against an innate or foreign noxient, such as a malignant cell or an invading microorganism. The immune system has been studied more in relation to recognizing and responding to exogenous noxients, such as microbial organisms, than it has in relation to indigenous malfunctions, such as cancer and certain autoimmune and immune-dysregulatory diseases, particularly since the latter may have both genetic as well as environmental components. The defenses against microbial organisms, such as bacteria, fungi, parasites, and viruses, are innate to the particular organism, with the immune system being programmed to recognize biochemical patterns of these microorganisms and to respond to attack them without requiring prior exposure to the microorganism. This innate immune system includes, for example, neutrophils, natural killer cells and monocytes/macrophages that can eradicate the invading microorganisms by direct engulfment and destruction.

The innate immune response is often referred to as a non-specific one that controls an invading external noxient until the more specific adaptive immune system can marshal specific antibodies and T cells (cf. Modlin et al., *N Engl J Med* 1999, 340:1834-1835; Das, *Crit. Care* 2000; 4:290-296). The nonspecific immune responses involve the lymphatic system and phagocytes. The lymphatic system includes the lymphocytes and macrophages. Macrophages can engulf, kill and dispose of foreign particles. Phagocytes include neutrophils and macrophages, which again ingest, degrade and dispose of debris, and have receptors for complement and antibody. In summary, the innate immune system provides a line of defense again certain antigens because of inherited characteristics.

In contrast, the adaptive, or acquired, immune system, is highly evolved and very specific in its responses. It is called an adaptive system because is occurs during the lifetime of an individual as an adaptation to infection with a pathogen. Adaptive immunity can be artificially acquired in response to a vaccine (antigens) or by administering antibodies, or can be naturally acquired by infection. The acquired immunity can be active, if an antibody was produced, or it can be passive, if exogenous antibody made form another source is injected.

The adaptive immune system produces antibodies specific to a given antigen. The simplest and most direct way in which antibodies provide protection is by binding to them and thereby blocking their access to cells that they may infect or destroy. This is known as neutralization. Binding by antibodies, however, is not sufficient to arrest the replication of bacteria that multiply outside cells. In this case, one role of antibody is to enable a phagocytic cell to ingest and destroy the bacterium. This is known as opsonization. The third function of antibodies is to activate a system of plasma proteins, known as complement. In many cases, the adaptive immune system confers lifelong protective immunity to re-infection with the same pathogen, because the adaptive immune system has a 'memory' of the antigens presented to it.

Antibody-mediated immunity is called humoral immunity and is regulated by B cells and the antibodies they produce. Cell-mediated immunity is controlled by T cells. Both humoral and cell-mediated immunity participate in protecting the host from invading organisms. This interplay can result in an effective killing or control of foreign organisms. Occasionally, however, the interplay can become erratic. In these cases, there is a dysregulation that can cause disease. Sometimes the disease is life-threatening, such as with septic shock and certain autoimmune disorders.

The B and T lymphocytes are critical components of a specific immune response. B cells are activated by antigen to engender clones of antigen-specific cells that mediate adaptive immunity. Most clones differentiate to plasma cells that secrete antibody, while a few clones form memory cells that revert to plasma cells. Upon subsequent re-infection, memory cells produce a higher level of antibody in a shorter period than in the primary response. Antibodies secreted by the plasma cells can play multiple roles in immunity, such as binding and neutralizing a foreign agent, acting as opsonins (IgG) to promote phagocytosis, directly affecting metabolism and growth of some organisms, engaging in antigen-antibody reactions that activate complement, causing phagocytosis and membrane attack complex, and/or engaging in antigen-antibody reactions that activate T cells and other killer cells.

T lymphocytes function as both helper cells and suppressor cells. Helper T cells induce antigen-specific B cells and effector T cells to proliferate and differentiate. Suppressor T cells interact with helper T cells to prevent an immune response or to suppress an ongoing one, or to regulate effector T cells. Cytotoxic T cells destroy antigen by binding to target cells. In a delayed-type hypersensitivity reaction, the T cells do not destroy antigen, but attract macrophages, neutrophils and other cells to destroy and dispose of the antigen.

T cells can detect the presence of intracellular pathogens because infected cells display on their surface peptide fragments derived from the pathogens' proteins. These foreign peptides are delivered to the cell surface by specialized host-cell glycoproteins, termed Major Histocompatibility Complex (MHC) molecules. The recognition of antigen as a small peptide fragment bound to a MHC molecule and displayed at the cell surface is one of the most distinctive features of T cells. There are two different classes of MHC molecules, know as MHC class I and MHC class II, that deliver peptides from different cellular compartments to the surface of the infected cell. Peptides from the cytosol are bound to MHC class I molecules which are expressed on the majority of nucleated cells and are recognized by CD8+ T cells. MHC class II molecules, in contrast, traffic to lysosomes for sampling endocytosed protein antigens which are presented to the CD4+ T cells (Bryant and Ploegh, *Curr Opin Immunol* 2004; 16:96-102).

CD8+ T cells differentiate into cytotoxic T cells, and kill the cell. CD4+ T cells differentiate into two types of effector T cells. Pathogens that accumulate in large numbers inside macrophage vesicles tend to stimulate the differentiation of $T_H1$ cells which activate macrophages and induce B cells to make IgG antibodies that are effective in opsonizing extracellular pathogens for uptake by phagocytes. Extracellular antigens tend to stimulate the production of $T_H2$ cells which initiate the humoral immune response by activating naïve antigen-specific B cells to produce IgM antibodies, inter alia.

The innate and adaptive immune systems interact, in that the cells of the innate immune system can express various molecules that can interact with or trigger the adaptive immune system by activating certain cells capable of producing immune factors, such as by activating T and B cells of the lymphatic series of leukocytes. The early induced but non-adaptive responses are important for two main reasons. First, they can repel a pathogen or, more often, control it until an adaptive immune response can be mounted. Second, these early responses influence the adaptive response in several ways. For example, the innate immune response produces cytokines and other inflammatory mediators that have profound effects on subsequent events, including the recruitment of new phagocytic cells to local sites of infection. Another effect of these mediators is to induce the expression of adhesion molecules on the endothelial cells of the local blood vessels, which bind to the surface of circulating monocytes and neutrophils and greatly increase their rate of migration of these cells out of the blood and into the tissues. These events all are included under the term inflammation, which is a feature of the innate immune system that forms part of the protective response at a localized site to isolate, destroy and remove a foreign material. This is followed by repair. Inflammation is divided into acute and chronic forms.

The immune system communicates via nonspecific tissue resistance factors. These include the interferons, which are proteins produced in response to viruses, endotoxins and certain bacteria. Interferons inhibit viral replication and activate certain host-defense responses. Infected cells produce interferon that binds the infected cells to other, neighboring cells, causing them to produce antiviral proteins and enzymes that interfere with viral gene transcription and proteins synthesis. Interferons can also affect normal cell growth and suppress cell-mediated immunity.

Complement is another nonspecific tissue resistance factor, and comprises plasma proteins and membrane proteins that mediate specific and non-specific defenses. Complement has two pathways, the classical pathway associated with specific defense, and the alternative pathway that is activated in the absence of specific antibody, and is thus non-specific. In the classical pathway, antigen-antibody complexes are recognized when C1 interacts with the Fc of the antibody, such as IgM and to some extent, IgG, ultimately causing mast cells to release chemotactic factors, vascular mediators and a respiratory burst in phagocytes, as one of many mechanisms. The key complement factors include C3a and C5a, which cause mast cells to release chemotactic factors such as histamine and serotonin that attract phagocytes, antibodies and complement, etc. Other key complement factors are C3b and C5b, which enhance phagocytosis of foreign cells, and C8 and C9, which induce lysis of foreign cells (membrane attack complex).

Cancer cells can escape immune surveillance by avoiding complement activation, especially by the expression of membrane-associated complement regulatory proteins, such as CD55 (decay-accelerating factor), CD46 (membrane cofactor protein), and CD59 (protecting, and it is believed that the over-expression of these proteins on cancer cell membranes protects these cancers from complement activation (Brasoveanu et al., *Lab Invest* 1996; 74:3342; Jarvis et al., *Int J Cancer* 1997; 71:1049-1055; Yu et al., *Clin Exp Immunol* 1999; 115:13-18; Murray et al., *Gynecol Oncol* 2000; 76:176-182; Donin et al., *Clin Exp Immunol* 2003; 131:254-263). Attempts have been made, unsuccessfully, to increase the susceptibility to complement-mediated lysis by use of neutralizing antibodies against CD46, CD55 and CD59 (Varsano et al., *Clin Exp Immunol* 1998; 113:173-182 Junnikkala et al *J Immunol* 2000; 164:6075-6081; Maenpaa et al., *Am J Pathol* 1996; 148:1139-1162; Gorter Lab Invest 1996; 74:1039-1049. In the latter study, CD46 and CD55 antibodies were, in contrast to CD59 antibodies, ineffective. This suggests that other targets, or the use of antibodies against multiple complement regulatory proteins, or against both complement regulatory proteins and other mediators of immunity may be required. This general failure contradicts the speculation of Fishelson et al. (*Mol Immunol* 2003: 40:109-123) and the suggestion from other studies that treatment of cancer patients with antibodies to membrane complement regulatory proteins in combination with anticancer complement-fixing antibodies will improve therapeutic efficacy, so there remains a need to elucidate how such strategies may best be implemented in cancer patients.

Gelderman et al. (*Mol Immunol* 2003; 40:13-23) reported that membrane-bound complement regulatory proteins (mCRP) inhibit complement activation by an immunotherapeutic mAb in a syngeneic rat colorectal cancer model. While the use of mAb against tumor antigens and mCRP overcame an observed effect of mCRP on tumor cells, there has been no direct evidence to support this approach. Still other attempts to use bispecific antibodies against CD55 and against a tumor antigen (G250 or EpCAM) have been suggested by Gelderman et al. (*Lab Invest* 2002; 82:483-493; *Eur J Immunol* 2002; 32:128-135) based on in vitro studies that showed a 2-13-fold increase in C3 deposition compared to use of the parental antitumor antibody. However, no results involving enhanced cell killing were reported. Jurianz et al. (*Immunopharmacology* 1999; 42:209-218) also suggested that combining treatment of a tumor with anti-HER2 antibodies in vitro could be enhanced by prior treatment with antibody-neutralization of membrane-complement-regulatory protein, but again no in vivo results were provided. Sier et al. (*Int J Cancer* 2004; 109:900-908) recently reported that a bispecific antibody made against an antigen expressed on renal cell carcinoma (Mab G250) and CD55 enhanced killing of renal cancer cells in spheroids when beta-glucan was added, suggesting that the presence of CR3-priming beta-glucan was obligatory.

Neutrophils, another cell involved in innate immune response, also ingest, degrade and dispose of debris. Neutrophils have receptors for complement and antibody. By means of complement-receptor bridges and antibody, the foreign noxients can be captured and presented to phagocytes for engulfment and killing.

Macrophages are white blood cells that are part of the innate system that continually search for foreign antigenic substances. As part of the innate immune response, macrophages engulf, kill and dispose of foreign particles. However, they also process antigens for presentation to B and T cells, invoking humoral or cell-mediated immune responses.

The dendritic cell is one of the major means by which innate and adaptive immune systems communicate (Reis e Sousa, *Curr Opin Immunol* 2004; 16:21-25). It is believed that these cells shape the adaptive immune response by the reactions to microbial molecules or signals. Dendritic cells capture, process and present antigens, thus activating CD4+ and CD8+ naïve T lymphocytes, leading to the induction of primary immune responses, and derive their stimulatory potency from expression of MHC class I, MHC class II, and accessory molecules, such as CD40, CD54, CD80, CD86, and T-cell activating cytokines (Steinman, *J Exp Hematol* 1996; 24:859-862; Banchereau and Steinman, *Nature* 1998; 392:245-252). These properties have made dendritic cells candidates for immunotherapy of cancers and infectious diseases (Nestle, *Oncogene* 2000; 19:673-679; Fong and Engleman, *Annu Rev Immunol* 2000; 18:245-273; Lindquist and Pisa, *Med Oncol* 2002; 19:197-211), and have been shown to induce antigen-specific cytotoxic T cells that result in strong immunity to viruses and tumors (Kono et al., *Clin Cancer Res* 2002; 8:394-40).

Also important for interaction of the innate and adaptive immune systems is the NK cell, which appears as a lymphocyte but behaves like a part of the innate immune system. NK cells have been implicated in the killing of tumor cells as well as essential in the response to viral infections (Lanier, *Curr Opin Immunol* 2003; 15:308-314; Carayannopoulos and Yokoyama, *Curr Opin Immunol* 2004; 16:26-33). Yet another important mechanism of the innate immune system is the activation of cytokine mediators that alert other cells of the mammalian host to the presence of infection, of which a key component is the transcription factor NF-κB (Li and Verma, *Nat Rev Immunol* 2002; 2:725-734).

As mentioned earlier, the immune system can overreact, resulting in allergies or autoimmune diseases. It can also be suppressed, absent, or destroyed, resulting in disease and death. When the immune system cannot distinguish between "self" and "nonself," it can attach and destroy cells and tissues of the body, producing autoimmune diseases, e.g., juvenile diabetes, multiple sclerosis, myasthenia gravis, systemic lupus erythematosus, rheumatoid arthritis, and immune thrombocytopenic purpura. Immunodeficiency disease results from the lack or failure of one or more parts of the immune system, and makes the individuals susceptible to diseases that usually do not affect individuals with a normal immune system. Examples of immunodeficiency disease are severe combined immunodeficiency disease (SCID) and acquired immunodeficiency disease (AIDS). The latter results from human immunodeficiency virus (HIV) and the former from enzyme or other inherited defects, such as adenosine deaminase deficiency.

A comprehensive description of the immune response and various aspects of immunity, autoimmune disorders, and immunodeficiency disorders is provided in Janeway et al., IMMUNOBIOLOGY: THE IMMUNE SYSTEM IN HEALTH AND DISEASE, Current Biology Publications, 1999; the Medical Encyclopedia of Medline Plus (nlm.nih.gov/medlineplus/encyclopedia.ahtml); and the internet site slic2.wsu.edu:82:hurlbert/micro101.pages/hap15.html, all of which are incorporated herein in their entirety by reference.

The application of immunotherapy to cancer involves a number of approaches to engage or exploit the immune system, such as adoptive transfer of anti-tumor-reactive T cells and the use of vaccines, as well as breaking tolerance to tumor self-antigens by inhibiting regulatory cells, and boosting T-cell immunity by use of various cytokines and so-called immune-enhancing molecules (Antonia et al., *Curr Opin Immunol* 2004; 16:130-136). Dendritic-cell vaccines have also been described. Direct and indirect (mediated by host effector cells) actions of antibodies administered to patients by targeting tumor-cell antigens/receptors have now entered the cancer therapy armamentarium, as exemplified by antibodies against CD20 and CD52 in the therapy of lymphomas and leukemia; anti-epidermal growth factor receptor (EGFR), the anti-HER2/neu variant, in the therapy of diverse solid tumors; and anti-vascular endothelium growth factor (VEGF) for the treatment of certain solid tumors. Although active when given alone, most of these show enhanced antitumor effects when combined with other treatment modalities, such as drugs and radiation. Using these tumor-targeting antibodies to deliver cytotoxic drugs or isotopes is still another method of immunotherapy that has entered the clinic. These and other methods of cancer immunotherapy have been reviewed in Huber and Wolfel, *J Cancer Res Clin Oncol* 2004; 130:367-374, incorporated herein in its entirety by reference. However, at best these approaches show reduction of tumor and improved survival in a proportion of the patients, most of whom eventually relapse, thus requiring other therapeutic interventions and different strategies to control their disease.

Sepsis is a major medical and economic burden to our society, affecting about 700,000 people annually in the United States, causing over 200,000 deaths annually, and costing approximately $16.7 billion per year (Angus et al., *Crit. Care Med* 2001; 29:1303-1310; Martin et al., *N Engl J Med* 2003; 348:1546-1554). The definition of sepsis has been difficult, and historically it was defined as the systemic host response to an infection. A discussion of the clinical definition of sepsis, encompassing systemic inflammatory response syndrome (SIRS), sepsis per se, severe sepsis, septic shock, and multiple organ dysfunction syndrome (MODS) is contained in Riedmann et al., *J Clin Invest* 2003; 112:460-467. Since it has been a common belief that sepsis is caused by the host's overwhelming reaction to the invading microorganisms, and that the patient is more endangered by this response that than the invading microorganisms, suppression of the immune and inflammatory responses was an early goal of therapy.

Numerous and diverse methods of immunosuppression or of neutralizing proinflammatory cytokines have proven to be unsuccessful clinically in patients with sepsis and septic shock anti-inflammatory strategies. (Riedmann, et al., cited above; Van Amersfoort et al. (*Clin Microbiol Rev* 2003; 16:379-414), such as general immunosuppression, use of nonsteroidal anti-inflammatory drugs, TNF-α antibody (infliximab) or a TNF—R:Fc fusion protein (etanercept), IL-1 (interleukin-1) receptor antagonist, or high doses of corticosteroids. However, a success in the treatment of sepsis in adults was the PROWESS study (Human Activated Protein C Worldwide Evaluation in Severe Sepsis (Bernard et al., *N Engl J Med* 2001; 344:699-709)), showing a lower mortality (24.7%) than in the placebo group (30.8%). This activated protein C agent probably inhibits both thrombosis and inflammation, whereas fibrinolysis is fostered. Van Amersfoort et al. state, in their review (ibid.) that: "Although the blocking or modulation of a number of other targets including complement and coagulation factors, neutrophil adherence, and NO release, are promising in animals, it remains to be determined whether these therapeutic approaches will be effective in humans." This is further emphasized in a review by Abraham, "Why immunomodulatory therapies have not worked in sepsis" (*Intensive Care Med* 1999; 25:556-566).

The immune system in sepsis is believed to have an early intense proinflammatory response after infection or trauma, leading to organ damage, but it is also believed that the innate immune system often fails to effectively kill invading microorganisms (Riedmann and Ward, *Expert Opin Biol Ther* 2003; 3:339-350). There have been some studies of macrophage migration inhibitory factor (MIF) in connection with sepsis that have shown some promise. For example, blockage of MIF or targeted disruption of the MIF gene significantly improved survival in a model of septic shock in mice (Calandra et al., *Nature Med* 2000; 6:164-170), and several lines of evidence have pointed to MIF as a potential target for therapeutic intervention in septic patients (Riedmann et al., cited above). Bucala et al. (U.S. Pat. No. 6,645,493 B1) have claimed that an anti-MIF antibody can be effective therapeutically for treating a condition or disease caused by cytokine-mediated toxicity, including different forms of sepsis, inflammatory diseases, acute respiratory disease syndrome, granulomatous diseases, chronic infections, transplant rejection, cachexia, asthma, viral infections, parasitic infections, malaria, and bacterial infections, which is incorporated herein in its entirety, including references. The use of anti-LPS (lipopolysaccharide) antibodies alone similarly has had mixed results in the treatment of patients with septic shock (Astiz and Rackow, *Lancet* 1998; 351:1501-1505; Van Amersfoort et al., *Clin Microbiol Rev* 2003; 16:379-414.

While both LPS and MIF have been pursued as targets in the treatment of sepsis and septic shock, approaches which target LPS or MIF alone by an antibody have not been sufficient to control the diverse manifestations of sepsis, especially in advanced and severe forms. Similarly, use of cytokines, such as IL-1, IL-6 (interleukin-6), IL-8 (interleukin-8), etc., as targets for antibodies for the treatment of sepsis and other cytokine-mediated toxic reactions, has not proven to be sufficient for a meaningful control of this disease. Therefore, in addition to the need to discover additional targets of the cytokine cascade involved in the endogenous response in sepsis, it has now been discovered that bi- and multi-functional antibodies targeting at least one cytokine or causative agent, such as MIF or lipopolysaccharide (LPS), is advantageous, especially when combined with the binding to a host cell (or its receptor) engaged in the inflammatory or immune response, such as T cells, macrophages or dendritic cells. Antibodies against an MHC class II invariant chain target, such as CD74, have been proposed by Bucala et al. (US 2003/0013122 A1), for treating MIF-regulated diseases, and Hansen et al. (US 2004/0115193 A1) proposed at least one CD74 antibody for treating an immune dysregulation disease, an autoimmune disease, organ graft rejection, and graft versus host disease. Hansen et al. describe the use of fusion proteins of anti-CD74 with other antibodies reacting with antigens/receptors on host cells such as lymphocytes and macrophages for the treatment of such diseases. However, combinations with targets other than CD74 are not suggested, and the disclosure focuses on a different method of immunotherapy. Similar targets are also useful to treat atherosclerotic plaques (Burger-Kentischer et al., *Circulation* 2002; 105: 1561-1566).

In the treatment of infectious, autoimmune, organ transplantation, inflammatory, and graft versus host (and other immunoregulatory) diseases, diverse and relatively non-specific cytotoxic agents are used to either kill or eliminate the noxient or microorganism, or to depress the host's immune response to a foreign graft or immunogen, or the host's production of antibodies against "self," etc. However, these usually affect the lymphoid and other parts of the hematopoietic system, giving rise to toxic effects to the bone marrow (hematopoietic) and other normal host cells.

Therefore, a need exists for improved, more selective therapy of cancer and diverse immune diseases, including sepsis and septic shock, inflammation, atherosclerosis, cachexia, graft versus host, and other immune dysregulatory disorders. The present invention is directed to overcoming or at least reducing the effects of one or more of the problems set forth above.

SUMMARY OF THE INVENTION

The present invention provides new and well-tolerated methods which use multispecific antagonists in the therapy of various inflammatory and immune-dysregulatory diseases, infectious diseases, pathologic angiogenesis and cancer. The multispecific antagonists are more effective than agents which react specifically with only one target associated with these conditions. The present invention provides a multispecific antagonist that reacts specifically with at least two different targets. The targets are selected from the group consisting of (A) proinflammatory effectors of the innate immune system, (B) coagulation factors, (C) complement factors and complement regulatory proteins, and (D) targets specifically associated with an inflammatory or immune-dysregulatory disorder or with a pathologic angiogenesis or cancer, wherein the latter target is not (A), (B), or (C). At least one of the targets is (A), (B) or (C). When the multispecific antagonist comprises a single multispecific antibody, then CD74 is excluded as a target of the antagonist. Furthermore, when the multispecific antagonist comprises a combination of separate antibodies, combinations are excluded where one of the antibodies targets a B-cell antigen and the other antibody targets a T-cell, plasma cell, macrophage or inflammatory cytokine. Combinations of separate antibodies are also excluded where one of the antibodies targets CD20 and the other antibody targets C3b or CD40.

The term "reacts specifically" encompasses not only the binding of an antibody or antibody fragment to an antigen, but also to the binding of a receptor to its cognate ligand. For example, a receptor for a proinflammatory effector of the innate immune system "reacts specifically" with its proinflammatory effector cognate ligand and thus falls within the scope of the present invention. In some embodiments, the multispecific antagonist is a combination of two separate antibodies. In other embodiments, it is a multispecific antibody, particularly a fusion protein.

In one embodiment, when the multispecific antagonist comprises a combination of separate antibodies, combinations are excluded where one of the antibodies targets CD19, CD20, CD21, CD22, CD23 or CD80 and the other antibody targets a complement factor. More particularly, when the multispecific antagonist comprises a combination of separate antibodies, combinations are excluded where one of the antibodies targets CD19, CD20, CD21, CD22, CD23 or CD80 and the other antibody targets C3b or CD40.

The proinflammatory effector of the innate immune system may be a proinflammatory effector cytokine, a proinflammatory effector chemokine or a proinflammatory effector receptor. Suitable proinflammatory effector cytokine include MIF, HMGB-1 (high mobility group box protein 1), TNF-α, IL-1, IL-4 (interleukin-4), IL-5 (interleukin-5), IL-6, IL-8, IL-12 (interleukin-12), IL-15 (interleukin-15), IL-17(interleukin-17), and IL-18 (interleukin-18). Examples of proinflammatory effector chemokines include CCL19, CCL21, IL-8, MCP-1, RANTES, MIP-1A, MIP-1B, ENA-78, MCP-1, IP-10, GROB, and Eotaxin. Proinflammatory effector receptors include IL-4R (interleukin-4 receptor), IL-6R (interleukin-6 receptor), IL-13R (interleukin-13 receptor), IL-15R (interleukin-15 receptor), IL-17R (interleukin-17 receptor) and IL-18R (interleukin-18 receptor).

The multispecific antagonist also may react specifically with at least one coagulation factor, particularly tissue factor (TF) or thrombin. In other embodiments, the multispecific antagonist reacts specifically with at least one complement factor or complement regulatory protein. In preferred embodiments, the complement factor is selected from the group consisting of C3, C5, C3a, C3b, and C5a. In these embodiments, target combinations preferably do not include those in which the other antibody targets CD19, CD20, CD21, CD22, CD23 or CD80 when the antagonist is a combination of separate antibodies. When the antagonist reacts specifically with a complement regulatory protein, the complement regulatory protein preferably is selected from the group consisting of CD46, CD55, CD59 and mCRP.

In one embodiment, the multispecific antagonist comprises two or more antibodies which differ in specificity, each of which reacts specifically with a different proinflammatory effector of the innate immune system. Alternatively, the multispecific antagonist comprises two or more antibodies that differ in specificity, each of which reacts specifically with a different coagulation factor. In another embodiment, the multispecific antagonist comprises two or more antibodies that differ in specificity, each of which reacts specifically with a different complement factor or complement regulatory protein. In yet other embodiments, the two or more antibodies react specifically with at least one proinflammatory effector of the innate immune system and with at least one coagulation factor, or with at least one proinflammatory effector of the innate immune system and with at least one complement factor or complement regulatory protein, or with at least one complement factor or complement regulatory protein and with at least one coagulation factor, respectively. Alternatively, the multispecific antagonist may react specifically with more than one proinflammatory effector of the innate immune system, or with more than one coagulation factor, or with more than one complement factor or complement regulatory protein.

The two or more antibodies may react specifically with more than one epitope of the same proinflammatory effector of the innate immune system or more than one epitope of the same coagulation factor or more than one epitope of the same complement factor or complement regulatory protein. In any of these embodiments, the multispecific antagonist additionally may react with a target specifically associated with an inflammatory or immune-dysregulatory disorder or with a pathologic angiogenesis or cancer, which target is not an (A), (B) or (C) target as defined above. In other embodiments, the multispecific antagonist reacts with a target specifically associated with an inflammatory or immune-dysregulatory disorder or with a pathologic angiogenesis or cancer, and with one or more (A), (B) or (C) targets as defined above. An example of a useful target for pathologic angiogenesis is Flt-1.

In any of the embodiments of the invention, the multispecific antagonist may be a multispecific antibody in which different arms of the antibody react with the different targets, subject to provisos elucidated herein. Such multispecific constructs can also have multivalency in any or all binding arms against the same antigen epitope in order to enhance binding to the antigen target, as described in Rossi (Patent Application WO 04094613A2).

The multispecific antagonist alternatively may comprise at least one soluble receptor, or at least an extracellular domain of at least one proinflammatory effector receptor. In one embodiment, the antagonist comprises at least one soluble receptor or at least an extracellular domain of a proinflammatory effector receptor fused to at least one antibody.

The multispecific antagonist may comprise at least one molecule reactive with a proinflammatory effector receptor. This molecule preferably is a natural antagonist for the proinflammatory effector receptor, or a fragment or mutant of the antagonist that interacts specifically with the receptor. In one embodiment, the natural antagonist is the natural IL-1 receptor antagonist, or a fragment or mutant of this antagonist.

The multispecific antagonist additionally may target dendritic cells, granulocytes, monocytes, macrophages, NK-cells, platelets, or endothelial cells. In some embodiments, the multispecific antagonist specifically reacts with at least one antigen or receptor of the adaptive immune system. In other embodiments, the multispecific antagonist specifically reacts with a cancer cell receptor or cancer-associated antigen, such as B-cell lineage antigens (CD19, CD20, CD21, CD22, CD23, etc.), VEGFR, EGFR, carcinoembryonic antigen (CEA), placental growth factor (PLGF), tenascin, HER-2/neu, EGP-1, EGP-2, CD25, CD30, CD33, CD38, CD40, CD45, CD52, CD74, CD80, CD138, NCA66, MUC1, MUC2, MUC3, MUC4, MUC16, IL-6, α-fetoprotein (AFP), A33, CA125, colon-specific antigen-p (CSAp), folate receptor, HLA-DR, human chorionic gonadotropin (HCG), Ia, EL-2, insulin-like growth factor (ILGF) and ILGF receptor, KS-1, Le(y), MAGE, necrosis antigens, PAM-4, prostatic acid phosphatase (PAP), Prl, prostate specific antigen (PSA), PSMA, S100, T101, TAC, TAG72, TRAIL receptors, and carbonic anhydrase IX. Flt-3, which targets proliferating myeloid bone marrow cells, also is a useful in identifying and treating certain cancers. Alternatively, the multispecific antagonist may react specifically with a target such as C5a, Factor H, FHL-1, LPS, IFNγ or B7, or with a target such as CD2, CD4, CD14, CD18, CD11a, CD19, CD20, CD22, CD23, CD25, CD29, CD38, CD40L, CD52, CD64, CD83, CD147 or CD154.

The multispecific antagonist may comprise a single active component, or it may comprise multiple active components. The embodiment comprising a single active component does not encompass mixtures of antibodies, which would by definition comprise two or more active components. Multispecific antagonists comprising more than one active component also may include secondary therapeutics that affect a component of the innate immune system, a component of the adaptive immune system, coagulation, infectious agents or cancer cells.

The multispecific antagonist may react specifically with targets or markers associated with specific diseases and conditions, such as infectious diseases, acute respiratory distress syndrome, septicemia or septic shock, graft versus host disease or transplant rejection, atherosclerosis, asthma, acne, giant cell arteritis, a granulomatous disease, a neuropathy, cachexia, a coagulopathy such as diffuse intravascular coagulation (DIC), or myocardial ischemia.

The multispecific antagonists are useful in treating conditions such as inflammatory or immune-dysregulatory disorders, pathologic angiogenesis or cancer, and infectious disease. Treatment comprises administering a therapeutically effective amount of the multispecific antagonist to a patient that has been diagnosed with one of the conditions. In one embodiment, the inflammatory or immune-dysregulatory disorder is not an autoimmune disease. The multispecific antagonist can be used to treat septicemia or septic shock, infectious disease (bacterial, viral, fungal, or parasitic), neuropathy, graft versus host disease or transplant rejection, acute respiratory distress syndrome, a granulomatous disease, asthma, atherosclerosis, acne, giant cell arteritis, coagulopathies such as diffuse intravascular coagulation (DIC), or cachexia. In other embodiments, the condition is an autoimmune disease, especially a Class III autoimmune diseases.

The multispecific antagonist also can be used to treat a pathologic angiogenesis or cancer. The cancer may be hematopoietic cancer, such as leukemia, lymphoma, or myeloma, etc. Alternatively, the cancer may be a solid tumor, such as a carcinoma, melanoma, sarcoma, glioma, etc.

The multispecific antagonist may be an immunoconjugate that comprises a therapeutic agent, such as a radionuclide, an immunomodulator, a hormone, a hormone antagonist, an enzyme, an enzyme inhibitor, oligonucleotide, a photoactive therapeutic agent, a cytotoxic agent, an antibody, an angiogenesis inhibitor, and a combination thereof. When the therapeutic agent is an oligonucleotide it may be an antisense oligonucleotide.

In other embodiments, the therapeutic agent is a cytotoxic agent, for example, a drug or a toxin. The drug may possess the pharmaceutical property selected from the group consisting of antimitotic, alkylating, antimetabolite, antiangiogenic, apoptotic, alkaloid, proteasome inhibitor, and antibiotic agents and combinations thereof. In certain embodiments, the drug is selected from the group consisting of nitrogen mustards, gemcitabine, ethylenimine derivatives, alkyl sulfonates, nitrosoureas, triazenes, folic acid analogs, anthracyclines, SN-38, taxanes, COX-2 inhibitors, pyrimidine analogs (e.g., 5-fluorouracil), purine analogs, antibiotics, enzymes, enzyme inhibitors, proteasome inhibitors, epipodophyllotoxins, platinum coordination complexes, vinca alkaloids, substituted ureas, methyl hydrazine derivatives, adrenocortical suppressants, hormone antagonists, endostatin, taxols, camptothecins, doxorubicins and their analogs, antimetabolites, alkylating agents, antimitotics, antiangiogenic, apoptotoic agents, methotrexate, CPT-11, and a combination thereof. The toxin may be derived from a source selected from the group comprising an animal, a plant, and a microbial source, and is preferably selected from the group consisting of ricin, abrin, alpha toxin, saporin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin.

In other embodiments the therapeutic agent is an immunomodulator, such as a cytokine, a stem cell growth factor, a lymphotoxin, a hematopoietic factor, a colony stimulating factor (CSF), an interferon (IFN), a stem cell growth factor, erythropoietin, thrombopoietin and a combination thereof. The lymphotoxin may be tumor necrosis factor (TNF), the hematopoietic factor may be an interleukin (IL), the colony stimulating factor may be granulocyte-colony stimulating factor (G-CSF) or granulocyte macrophage-colony stimulating factor (GM-CSF)), the interferon may be interferon-α, β or γ, and the stem cell growth factor may be S1 factor. Preferably the immunomodulator comprises IL-1, IL-2, IL-3, IL-6, IL-10, IL-12, IL-17, IL-18, IL-21, interferon-γ, TNF-α, or a combination thereof.

Alternatively, the therapeutic agent is a radionuclide. Preferably the radionuclide has an energy between 60 and 700 keV, an preferably is selected from the group consisting of $^{32}P$, $^{33}P$, $^{47}Sc$, $^{125}I$, $^{131}I$, $^{86}Y$, $^{90}Y$, $^{186}Re$, $^{188}Re$, $^{189}Re$, $^{64}Cu$, $^{67}Cu$, $^{67}Ga$, $^{111}In$, $^{111}Ag$, $^{142}Pr$, $^{153}Sm$, $^{161}Tb$, $^{166}Dy$, $^{166}Ho$, $^{177}Lu$, $^{198}Au$, $^{211}At$, $^{212}Pb$, $^{212}Bi$, $^{213}Bi$, $^{223}Ra$ and $^{225}Ac$, and combinations thereof.

In other embodiments, the therapeutic agent is a photoactive therapeutic agent, such as a chromogen or and dye. The therapeutic agent also may be an enzyme. The enzyme preferably is selected from the group comprising malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

The multispecific antagonist may comprise a diagnostic/detection agent. The diagnostic/detection agent may be selected from the group consisting of a diagnostic radionuclide, a contrast agent, a fluorescent label, and a photoactive agent.

The invention also provides a method of diagnosing or detecting a condition selected from an inflammatory or immune-dysregulatory disorder, a pathologic angiogenesis or cancer, and an infectious disease, comprising administering a diagnostically effective amount of a multispecific antagonist according to the invention to a patient that is suspected of having such a condition; permitting the multispecific antagonist to accrete at target sites; waiting for circulating multispecific antibody to clear from the bloodstream or using a clearing agent; and locating the sites of accretion of said labeled multispecific antagonist by detecting elevated levels of said labeled multispecific antagonist at such sites with a detection means.

Another method of diagnosing or detecting a condition selected from an inflammatory or immune-dysregulatory disorders, a pathologic angiogenesis or cancer, and an infectious disease, comprises administering a diagnostically effective amount of a multispecific antagonist according to the invention that includes a hapten binding site, to a patient that is suspected of having such a condition; permitting the multispecific antagonist to accrete at target sites; waiting for circulating multispecific antibody to clear from the bloodstream; administering to said subject a hapten labeled with a diagnostic/detection agent; allowing the labeled hapten to bind to the hapten binding site of said multispecific antagonist; and locating the sites of accretion of said multispecific antagonist by detecting elevated levels of said multispecific antagonist bound to said labeled hapten at such sites with a detection means.

The present invention also provides a method of treating a condition selected from an inflammatory or immune-dysregulatory disorders, a pathologic angiogenesis or cancer, and an infectious disease, comprising administering a therapeutically effective amount of a multispecific antagonist according to the invention, that includes a hapten binding site, to a patient that is suspected of having such a condition; permitting the multispecific antagonist to accrete at target sites; waiting for circulating multispecific antibody to clear from the bloodstream; administering to said subject a hapten that comprises a therapeutic agent; and allowing the hapten with the therapeutic agent to bind to the hapten binding site of said multispecific antagonist.

DETAILED DESCRIPTION OF SPECIFIC EMBODIMENTS

Definitions

In the description that follows, and in documents incorporated by reference, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent when the promoter is a constitutive promoter.

An isolated DNA molecule is a fragment of DNA that is not integrated in the genomic DNA of an organism. For example, a cloned antibody gene is a DNA fragment that has been separated from the genomic DNA of a mammalian cell. Another example of an isolated DNA molecule is a chemically synthesized DNA molecule that is not integrated in the genomic DNA of an organism.

An enhancer is a DNA regulatory element that can increase the efficiency of transcription, regardless of the distance or orientation of the enhancer relative to the start site of transcription.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

As used herein, antibody encompasses naked antibodies and conjugated antibodies and antibody fragments, which may be monospecific or multispecific. It includes recombinant antibodies, such as chimeric antibodies, humanized antibodies and fusion proteins.

A chimeric antibody is a recombinant protein that contains the variable domains and complementary determining regions derived from a rodent antibody, while the remainder of the antibody molecule is derived from a human antibody.

Humanized antibodies are recombinant proteins in which murine complementarity determining regions of a monoclonal antibody have been transferred from heavy and light variable chains of the murine immunoglobulin into a human variable domain. A humanized murine antibody (CDR-grafted) has the murine CDRs grafted into the FRs of a human IgG. The CDR-grafted human variable chains are fused to the constant regions of a human antibody to obtain an intact humanized IgG.

Human antibodies are antibodies that either are isolated from humans and then grown out in culture or are made using animals whose immune systems have been altered so that they respond to antigen stimulation by producing human antibodies.

An antibody fragment is a portion of an intact antibody such as $F(ab')_2$, $F(ab)_2$, Fab', Fab, Fv, sFv and the like. Regardless of structure, an antibody fragment binds with the same antigen that is recognized by the full-length antibody. For example, an anti-CD20 monoclonal antibody fragment binds with an epitope of CD20. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

Antibody fragments produced by limited proteolysis of wildtype antibodies are called proteolytic antibody fragments. These include, but are not limited to, the following:

$F(ab')_2$ fragments are released from an antibody by limited exposure of the antibody to a proteolytic enzyme, e.g., pepsin or ficin. A $F(ab')_2$ fragment comprises two "arms," each of which comprises a variable region that is directed to and specifically binds a common antigen. The two Fab' molecules are joined by interchain disulfide bonds in the hinge regions of the heavy chains; the Fab' molecules may be directed toward the same (bivalent) or different (bispecific) epitopes.

Fab' fragments contain a single anti-binding domain comprising a Fab and an additional portion of the heavy chain through the hinge region.

Fab'-SH fragments are typically produced from $F(ab')_2$ fragments, which are held together by disulfide bond(s) between the H chains in an $F(ab')_2$ fragment. Treatment with a mild reducing agent such as, by way of non-limiting example, beta-mercaptoethylamine, breaks the disulfide bond(s), and two Fab' fragments are released from one $F(ab')_2$ fragment. Fab'-SH fragments are monovalent and monospecific.

Fab fragments (i.e., an antibody fragment that contains the antigen-binding domain and comprises a light chain and part of a heavy chain bridged by a disulfide bond) are produced by papain digestion of intact antibodies. A convenient method is to use papain immobilized on a resin so that the enzyme can be easily removed and the digestion terminated. Fab fragments do not have the disulfide bond(s) between the H chains present in an F(ab')$_2$ fragment.

Single-chain antibodies are one type of antibody fragment. The term single chain antibody is often abbreviated as "scFv" or "sFv." These antibody fragments are produced using molecular genetics and recombinant DNA technology. A single-chain antibody consists of a polypeptide chain that comprises both a $V_H$ and a $V_L$ domains which interact to form an antigen-binding site. The $V_H$ and $V_L$ domains are usually linked by a peptide of 10 to 25 amino acid residues. The term "single-chain antibody" further includes, but is not limited to, a disulfide-linked Fv (dsFv) in which two single-chain antibodies (each of which may be directed to a different epitope) are linked together by a disulfide bond; a bispecific sFv in which two discrete scFvs of different specificity is connected with a peptide linker; a diabody (a dimerized sFv formed when the $V_H$ domain of a first sFv assembles with the $V_L$ domain of a second sFv and the $V_L$ domain of the first sFv assembles with the $V_H$ domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Thus, when making a scFv, diabody, or triabody, the constant regions are not used, and the humanized variable regions are joined with a linker.

Complementary determining region peptides or CDR peptides are another form of an antibody fragment. A CDR peptide (also known as "minimal recognition unit") is a peptide corresponding to a single complementarity-determining region (CDR), and can be prepared by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2:106, 1991.

In cysteine-modified antibodies, a cysteine amino acid is inserted or substituted on the surface of antibody by genetic manipulation and used to conjugate the antibody to another molecule via, e.g., a disulfide bridge. Cysteine substitutions or insertions for antibodies have been described (see U.S. Pat. No. 5,219,996). Methods for introducing Cys residues into the constant region of the IgG antibodies for use in site-specific conjugation of antibodies are described by Stimmel et al. (*J. Biol. Chem.* 275:330445-30450, 2000).

As used herein, a therapeutic agent is a molecule or atom, which is conjugated to an antibody moiety to produce a conjugate which is useful for therapy. These can be active when given unconjugated to an antibody, such as with $^{131}$I in thyroid neoplasms, and various cytotoxic drugs in cancer, autoimmune diseases, graft versus host disease, and in the immunosuppression induced for organ transplantation, etc. Examples of therapeutic agents include a therapeutic radionuclide, a boron compound, an immunomodulator, a hormone, a hormone antagonist, an enzyme, oligonucleotides, an enzyme inhibitor, a photoactive therapeutic agent, a cytotoxic agent, and an angiogenesis inhibitor, and a combination thereof, and these are described in US Published Application no. 2004 0057902. Preferred therapeutic radioisotopes include beta, alpha, and Auger emitters, with a keV range of 80-500 keV. Exemplary therapeutic radioisotopes include $^{225}$Ac, $^{177}$Lu, $^{198}$Au, $^{32}$P, $^{125}$I, $^{131}$I, $^{90}$Y, $^{186}$Re, $^{188}$Re, $^{67}$Cu, $^{67}$Ga, $^{111}$In, and $^{211}$At.

A diagnostic/detection agent is a molecule or atom which is administered conjugated to a multispecific antagonist according to the invention, i.e., antibody or antibody fragment, or subfragment, and is useful in diagnosing a disease by locating the cells containing the antigen. Useful diagnostic/detection agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI), as well as for ultrasound and computed tomography.

A naked antibody is an antibody which is not conjugated with a therapeutic agent. Naked antibodies include both polyclonal and monoclonal antibodies, as well as certain recombinant antibodies, such as chimeric and humanized antibodies.

A conjugated antibody is an antibody or antibody fragment that is conjugated to a diagnostic or therapeutic agent.

A multispecific antibody is an antibody which can bind simultaneously to at least two targets which are of different structure, e.g., two different antigens, two different epitopes on the same antigen, or a hapten and/or an antigen or epitope. Two or more of the binding arms may be directed to the same or different epitopes of the same antigen, thus constituting multivalency in addition to multispecificity.

A bispecific antibody is an antibody or antibody fragment construct which can bind simultaneously to two targets which are of different structure.

A fusion protein is a recombinantly produced antigen-binding molecule in which two or more different single-chain antibody or antibody fragment segments with the same or different specificities are linked. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

An infectious disease is one that is caused by a microbe or parasite.

A microbe is a virus, bacteria, *rickettsia*, mycoplasma, fungi or like microorganisms.

A parasite is an infectious, generally microscopic or very small, multicellular invertebrate, protozoan, or an ovum or juvenile form thereof, which is susceptible to antibody-induced clearance or lytic or phagocytic destruction.

Multispecific Antagonists

The present invention provides multispecific antagonists that react specifically with at least two different targets. The different targets include proinflammatory effectors of the innate immune system, coagulation factors, complement factors and complement regulatory proteins, and targets specifically associated with an inflammatory or immune-dysregulatory disorder, with an infectious pathogen, or with a pathologic angiogenesis or cancer, wherein this latter class of target is not a proinflammatory effector of the immune system or a coagulation factor. When the multispecific antagonist reacts specifically with a target associated with an inflammatory or immune-dysregulatory disorder, with a pathologic angiogenesis or cancer, or with an infectious disease, it also binds specifically with at least one proinflammatory effector of the immune system, at least one coagulation factor, or at least one complement factor or complement regulatory protein. Thus, the multispecific antagonist contains at least one binding specificity related to the diseased cell, pathologic angiogenesis or cancer, or infectious disease, and at least one specificity to a component of the immune system, such as a receptor or antigen of B cells, T cells, neutrophils, monocytes and macrophages, and dendritic cells, or modulators of coagulation, such as thrombin or tissue factor, or proinflammatory cytokines, such as IL-1, IL-6, IL-10, HMGB-1, and MIF.

When the multispecific antagonist comprises a single multispecific antibody, then CD74 is excluded as a target of said antagonist. Furthermore, when the multispecific antagonist comprises a combination of separate antibodies, combinations are excluded where one of the components targets a B-cell antigen, and the other component targets a T-cell, plasma cell, macrophage or inflammatory cytokine.

The present invention is directed to compositions that contain multifunctional proteins and antibodies, and fragments thereof, as well as to compositions that contain a combination of multiple separate proteins or antibodies, or fragments thereof. Thus, in one embodiment, the multispecific antagonist is an antibody fusion protein or a heteroconjugate. In an alternative embodiment, the multispecific antagonist is an antibody mixture that contains at least two separate antibodies that bind to the different targets. In this embodiment, two or more antibodies or antibody conjugates are given simultaneously or sequentially. The multispecific antagonist can be naked, but can also be conjugated to a diagnostic imaging agent (e.g., isotope, radiological contrast agent,) or to a therapeutic agent, including a radionuclide, a boron compound, an immunomodulator, a hormone, a hormone antagonist, an enzyme, oligonucleotides, an enzyme inhibitor, a photoactive therapeutic agent, a cytotoxic agent, an angiogenesis inhibitor, and a combination thereof. The binding of the multispecific antagonist to a target can down-regulate or otherwise affect an immune cell function, but the multispecific antagonist also may bind to other targets that do not directly affect immune cell function. For example, an anti-granulocyte antibody, such as against CD66 or CEACAM6 (e.g., NCA90 or NCA95), can be used to target granulocytes in infected tissues, and can also be used to target cancers that express CEACAM6.

In one embodiment, the therapeutic agent is an oligonucleotide. For example, the oligonucleotide can be an antisense oligonucleotide, or a double stranded interfering RNA (RNAi) molecule. The oligonucleotide can be against an oncogene like bcl-2 or p53. An antisense molecule inhibiting bcl-2 expression is described in U.S. Pat. No. 5,734,033. It may be conjugated to, or form the therapeutic agent portion of a multispecific antagonist of the present invention. Alternatively, the oligonucleotide may be administered concurrently or sequentially with the multispecific antagonist of the present invention.

In another embodiment, the therapeutic agent is a boron addend, and treatment entails irradiation with thermal or epithermal neutrons after localization of the therapeutic agent. The therapeutic agent also may be a photoactive therapeutic agent, particularly one that is a chromogen or a dye.

In a preferred embodiment, the therapeutic agent is a cytotoxic agent, such as a drug or toxin. Also preferred, the drug is selected from the group consisting of nitrogen mustards, ethylenimine derivatives, alkyl sulfonates, nitrosoureas, gemcitabine, triazenes, folic acid analogs, anthracyclines, taxanes, COX-2 inhibitors, pyrimidine analogs, purine analogs, antibiotics, enzymes, enzyme inhibitors, epipodophyllotoxins, platinum coordination complexes, vinca alkaloids, substituted ureas, methyl hydrazine derivatives, adrenocortical suppressants, hormone antagonists, endostatin, taxols, SN-38, camptothecins, doxorubicins and their analogs, antimetabolites, alkylating agents, antimitotics, antiangiogenic, apoptotoic agents, methotrexate, CPT-11, and a combination thereof.

In another preferred embodiment, the therapeutic agent is a toxin derived from a source selected from the group comprising an animal, a plant, and a microbial source. Preferred toxins include ricin, abrin, alpha toxin, saporin, ribonuclease (RNase), DNase I, Staphylococcal enterotoxin-A, pokeweed antiviral protein, gelonin, diphtherin toxin, *Pseudomonas* exotoxin, and *Pseudomonas* endotoxins.

The therapeutic agent may be an immunomodulator, such as a cytokine, a stem cell growth factor, a lymphotoxin, a hematopoietic factor, a colony stimulating factor (CSF), an interferon (IFN), a stem cell growth factor, erythropoietin, thrombopoietin and a combination thereof. said lymphotoxin is tumor necrosis factor (TNF). The hematopoietic factor may be an interleukin (IL), the colony stimulating factor may be a granulocyte-colony stimulating factor (G-CSF) or granulocyte macrophage-colony stimulating factor (GM-CSF)), the interferon may be interferons-α, β or γ, and the stem cell growth factor may be SI factor. Alternatively, the immunomodulator may comprise IL-1, IL-2, IL-3, IL-6, IL-10, IL-12, IL-17, IL-18, IL-21, interferon-γ, TNF-α, or a combination thereof.

Preferred therapeutic radionuclides include beta, alpha, and Auger emitters, with a keV range of 80-500 keV. Exemplary therapeutic radioisotopes include $^{32}$P, $^{33}$P, $^{47}$Sc, $^{125}$I, $^{131}$I, $^{86}$Y, $^{90}$Y, $^{186}$Re, $^{188}$Re, $^{189}$Re, $^{64}$Cu, $^{67}$Cu, $^{67}$Ga, $^{111}$I, $^{111}$Ag, $^{142}$Pr, $^{153}$Sm, $^{166}$Dy, $^{166}$Ho, $^{177}$Lu, $^{198}$Au, $^{211}$At, $^{212}$Pb, $^{212}$Bi, $^{213}$Bi, $^{223}$Ra and $^{225}$Ac, and combinations thereof. Exemplary photoactive therapeutic agents are selected from the group comprising chromogens and dyes.

Still preferred, the therapeutic agent is an enzyme selected from the group comprising malate dehydrogenase, staphylococcal nuclease, delta-V-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase.

The multispecific antagonist may bind specifically to at least one proinflammatory effector cytokine, proinflammatory effector chemokine, or proinflammatory effector receptor. Proinflammatory effector cytokines to which the multispecific antagonist may bind include, but are not restricted to, MIF, HMGB-1, TNF-α (tumor necrosis factor alpha), IL-1, IL-4, IL-5, IL-6, IL-8, IL-12, IL-15, IL-17 and IL-18. Proinflammatory effector chemokines include, but are not restricted to, CCL19, CCL21, IL-8, MCP-1 (monocyte chemotactic protein 1), RANTES, MIP-1A (macrophage inflammatory protein 1A), MIP-1B (macrophage inflammatory protein 1B), ENA-78 (epithelial neutrophil activating peptide 78), IP-10, GROB (GRO beta), and Eotaxin. Proinflammatory effector receptors include, but are not restricted to, IL4R, IL-6R, IL-13R, IL-15R, IL-17R and IL-18R. The multispecific antagonist also may react specifically with at least one coagulation factor, such as tissue factor or thrombin. The lymphokines/cytokines react with their receptors on the immune cells to effect activation, and antibodies can block activation by neutralizing the lymphokine/cytokine. Alternatively, antibodies can react with the lymphokine/cytokine receptors to block activation.

The different targets to which the multispecific antagonist binds specifically may be from the same or different classes of effectors and coagulation factors. For example, the two or more different targets to which the antagonist binds specifically may be selected from the same class of effectors or coagulation factors, such as two or more different proinflammatory effector cytokines, two or more different proinflammatory effector chemokines, two or more different proinflammatory effector receptors, or two or more coagulation factors. Alternatively, the two or more different targets may be selected from different classes of effectors and coagulation factors. For example, one target may be a proinflammatory effector of the innate immune system and one target may be a coagulation factor. Or the antagonist may react specifically with two different classes of proinflammatory effectors, such as at least one proinflammatory effector cytokine and at least one proinflammatory effector chemokine, at least one proinflammatory effector cytokine and at least one proinflammatory effector receptor, or at least one proinflammatory effector chemokine and at least one proinflammatory effector receptor. It may also be the case that the two different targets with which the multispecific antagonist reacts specifically are more than one epitope of the same proinflammatory effector of the innate immune system or more than one epitope of the same coagulation factor.

Thus, "two different targets" can refer to two different antigens, or to two different epitopes of the same antigen. Multiple antibodies may be used against the same antigen, thus increasing valency. For example, when targeting MIF or HMGB-1, particularly for the treatment of sepsis, some cancers, and atherosclerotic plaques, two antibodies binding to two identical epitopes of the targets can be fused with another antibody having one or more binding arms to a different antigen, such as an HLA class II invariant chain antigen, such as CD74. These are examples of bispecific or bifunctional antibodies that bind to two different antigens, e.g., antibodies to MIF and CD74; antibodies to HMGB-1 and CD74. Trispecific and multispecific fusion proteins can also be made and used, thus targeting more than two antigens or receptor molecules. These can have a single binding arm to each antigen or epitope, or more than one, thus resulting in multivalency.

When a proinflammatory effector receptor is targeted, in a preferred embodiment the actual target may be an extracellular domain of the proinflammatory effector receptor. This extracellular domain of the proinflammatory effector receptor may be fused to an antibody. More particularly, the proinflammatory effector may be a soluble receptor or receptor ligand which is fused to an antibody. In an alternative embodiment, the multispecific antagonist may comprise at least one molecule reactive with a proinflammatory effector receptor. This molecule may be a natural antagonist for said proinflammatory effector receptor, or a fragment or mutant of this antagonist that interacts specifically with the receptor. In a preferred embodiment, the natural antagonist is the natural IL-1 receptor antagonist, or a fragment or mutant of this antagonist.

One of the at least two different targets to which the multispecific antagonist binds specifically may be a target that is not a proinflammatory effector of the immune system or a coagulation factor. In this case the multispecific antagonist also binds specifically with at least one proinflammatory effector of the immune system or at least one coagulation factor. In one embodiment, this at least one other target is an antigen or receptor of the adaptive immune system. In other embodiments, the at least one other target of the multispecific antagonist targets cells of the innate immune system, such as granulocytes, monocytes, macrophages, dendritic cells, and NK-cells. Other targets include platelets and endothelial cells. Yet another group of targets is the group consisting of C5a, LPS, IFNγ and B7. A further group of suitable targets include CD2, CD4, CD14, CD18, CD11a, CD20, CD22, CD23, CD25, CD29, CD38, CD40L, CD52, CD64, CD83, CD147, and CD154. The CDs are targets on immune cells, which can be blocked by antibodies to prevent an immune cell response. CD83 is particularly useful as a marker of activated dendritic cells (Cao et al., *Biochem J.*, Aug. 23, 2004 (Epub ahead of print); Zinser et al., *J. Exp Med* 200(3):345-51 (2004)).

Certain targets are of particular interest, such as MIF, HMGB-1, TNF-α, the complement factors and complement regulatory proteins, and the coagulation factors. MIF is a pivotal cytokine in of the innate immune system and plays an important part in the control of inflammatory responses. Originally described as a T lymphocyte-derived factor that inhibited the random migration of macrophages, the protein known as macrophage migration inhibitory factor (MIF) was an enigmatic cytokine for almost 3 decades. In recent years, the discovery of MIF as a product of the anterior pituitary gland and the cloning and expression of bioactive, recombinant MIF protein have led to the definition of its critical biological role in vivo. MIF has the unique property of being released from macrophages and T lymphocytes that have been stimulated by glucocorticoids. Once released, MIF overcomes the inhibitory effects of glucocorticoids on TNF-α, IL-1 beta, IL-6, and IL-8 production by LPS-stimulated monocytes in vitro and suppresses the protective effects of steroids against lethal endotoxemia in vivo. MIF also antagonizes glucocorticoid inhibition of T-cell proliferation in vitro by restoring IL-2 and IFN-gamma production. MIF is the first mediator to be identified that can counter-regulate the inhibitory effects of glucocorticoids and thus plays a critical role in the host control of inflammation and immunity. MIF is particularly useful in treating cancer, pathological angiogenesis, and sepsis or septic shock.

HMGB-1, a DNA binding nuclear and cytosolic protein, is a proinflammatory cytokine released by monocytes and macrophages that have been activated by IL-1β, TNF, or LPS. Via its B box domain, it induces phenotypic maturation of DCs. It also causes increased secretion of the pro inflammatory cytokines IL-1 alpha, IL-6, IL-8, IL-12, TNF-α and RANTES. HMGB-1 released by necrotic cells may be a signal of tissue or cellular injury that, when sensed by Dcs, induces and or enhances an immune reaction. Palumbo et al. report that HMGB-1 induces mesoangioblast migration and proliferation (*J Cell Biol*, 164:441-449 (2004)).

HMGB-1 is a late mediator of endotoxin-induced lethality that exhibits significantly delayed kinetics relate to TNF and IL-1 beta. Experimental therapeutics that target specific early inflammatory mediators such as TNF and IL-1 beta alone have not proven efficacious in the clinic, but multispecific antagonists according to the present invention can improve response by targeting both early and late inflammatory inflammatory mediators.

Multispecific antagonists that target HMGB-1 are especially useful in treating arthritis, particularly collagen-induced arthritis. Multispecific antagonists comprising HMGB-1 also are useful in treating sepsis and/or septic shock. Yang et al., *PNAS USA* 101:296-301 (2004); Kokkola et al., *Arthritis Rheum*, 48:2052-8 (2003); Czura et al., *J Infect Dis,* 187 Suppl 2:S391-6 (2003); Treutiger et al., *J Intern Med,* 254:375-85 (2003).

TNF-α is an important cytokine involved in systemic inflammation and the acute phase response. TNF-α is released by stimulated monocytes, fibroblasts, and endothelial cells. Macrophages, T-cells and B-lymphocytes, granulocytes, smooth muscle cells, eosinophils, chondrocytes, osteoblasts, mast cells, glial cells, and keratinocytes also produce TNF-α after stimulation. Its release is stimulated by several other mediators, such as interleukin-1 and bacterial endotoxin, in the course of damage, e.g., by infection. It has a number of actions on various organ systems, generally together with interleukins-1 and -6. One of the actions of TNF-α is appetite suppression; hence multispecific antagonists for treating cachexia preferably target TNF-α. It also stimulates the acute phase response of the liver, leading to an increase in C-reactive protein and a number of other mediators. It also is a useful target when treating sepsis or septic shock.

The complement system is a complex cascade involving proteolytic cleavage of serum glycoproteins often activated by cell receptors. The "complement cascade" is constitutive and non-specific but it must be activated in order to function. Complement activation results in a unidirectional sequence of enzymatic and biochemical reactions. In this cascade, a specific complement protein, C5, forms two highly active, inflammatory byproducts, C5a and C5b, which jointly activate white blood cells. This in turn evokes a number of other inflammatory byproducts, including injurious cytokines, inflammatory enzymes, and cell adhesion molecules. Together, these byproducts can lead to the destruction of tissue seen in many inflammatory diseases. This cascade ultimately results in induction of the inflammatory response, phagocyte chemotaxis and opsonization, and cell lysis.

The complement system can be activated via two distinct pathways, the classical pathway and the alternate pathway. Most of the complement components are numbered (e.g., C1, C2, C3, etc.) but some are referred to as "Factors." Some of the components must be enzymatically cleaved to activate their function; others simply combine to form complexes that are active. Active components of the classical pathway include C1q, C1r, C1s, C2a, C2b, C3a, C3b, C4a, and C4b. Active components of the alternate pathway include C3a, C3b, Factor B, Factor Ba, Factor Bb, Factor D, and Properdin. The last stage of each pathway is the same, and involves component assembly into a membrane attack complex. Active components of the membrane attack complex include C5a, C5b, C6, C7, C8, and C9n.

While any of these components of the complement system can be targeted by a multispecific antagonist according to the invention, certain of the complement components are preferred. C3a, C4a and C5a cause mast cells to release chemotactic factors such as histamine and serotonin, which attract phagocytes, antibodies and complement, etc. These form one group of preferred targets according to the invention. Another group of preferred targets includes C3b, C4b and C5b, which enhance phagocytosis of foreign cells. Another preferred group of targets are the predecessor components for these two groups, i.e., C3, C4 and C5. C5b, C6, C7, C8 and C9 induce lysis of foreign cells (membrane attack complex) and form yet another preferred group of targets.

Complement C5a, like C3a, is an anaphylatoxin. It mediates inflammation and is a chemotactic attractant for induction of neutrophilic release of antimicrobial proteases and oxygen radicals. Therefore, C5a and its predecessor C5 are particularly preferred targets. By targeting C5, not only is C5a affected, but also C5b, which initiates assembly of the membrane-attack complex. Thus, CS is another preferred target. C3b, and its predecessor C3, also are preferred targets, as both the classical and alternate complement pathways depend upon C3b. Three proteins affect the levels of this factor, C1 inhibitor, protein H and Factor I, and these are also preferred targets according to the invention. Complement regulatory proteins, such as CD46, CD55, and CD59, may be targets to which the multispecific antagonists bind.

Coagulation factors also are preferred targets according to the invention, particularly tissue factor (TF) and thrombin. TF is also known also as tissue thromboplastin, CD142, coagulation factor III, or factor III. TF is an integral membrane receptor glycoprotein and a member of the cytokine receptor superfamily. The ligand binding extracellular domain of TF consists of two structural modules with features that are consistent with the classification of TF as a member of type-2 cytokine receptors. TF is involved in the blood coagulation protease cascade and initiates both the extrinsic and intrinsic blood coagulation cascades by forming high affinity complexes between the extracellular domain of TF and the circulating blood coagulation factors, serine proteases factor VII or factor VIIa. These enzymatically active complexes then activate factor IX and factor X, leading to thrombin generation and clot formation.

TF is expressed by various cell types, including monocytes, macrophages and vascular endothelial cells, and is induced by IL-1, TNF-α or bacterial lipopolysaccharides. Protein kinase C is involved in cytokine activation of endothelial cell TF expression. Induction of TF by endotoxin and cytokines is an important mechanism for initiation of disseminated intravascular coagulation seen in patients with Gram-negative sepsis. TF also appears to be involved in a variety of non-hemostatic functions including inflammation, cancer, brain function, immune response, and tumor-associated angiogenesis. Thus, multispecific antagonists that target TF are useful not only in the treatment of coagulopathies, but also in the treatment of sepsis, cancer, pathologic angiogenesis, and other immune and inflammatory dysregulatory diseases according to the invention. A complex interaction between the coagulation pathway and the cytokine network is suggested by the ability of several cytokines to influence TF expression in a variety of cells and by the effects of ligand binding to the receptor. Ligand binding (factor VIIa) has been reported to give an intracellular calcium signal, thus indicating that TF is a true receptor.

Thrombin is the activated form of coagulation factor II (prothrombin); it converts fibrinogen to fibrin. Thrombin is a potent chemotaxin for macrophages, and can alter their production of cytokines and arachidonic acid metabolites. It is of particular importance in the coagulopathies that accompany sepsis. Numerous studies have documented the activation of the coagulation system either in septic patients or following LPS administration in animal models. Despite more than thirty years of research, the mechanisms of LPS-induced liver toxicity remain poorly understood. It is now clear that they involve a complex and sequential series of interactions between cellular and humoral mediators. In the same period of time, gram-negative systemic sepsis and its sequallae have become a major health concern, attempts to use monoclonal antibodies directed against LPS or various inflammatory mediators have yielded only therapeutic failures, as noted elsewhere herein. Multispecific antagonists according to the invention that target both thrombin and at least one other target address the clinical failures in sepsis treatment.

In other embodiments, the multispecific antagonists bind to a MHC class I, MHC class II or accessory molecule, such as CD40, CD54, CD80 or CD86. The multispecific antagonist also may bind to a T-cell activation cytokine, or to a cytokine mediator, such as NF-κB.

In certain embodiments, one of the at least two different targets may be a cancer cell receptor or cancer-associated antigen, particularly one that is selected from the group consisting of B-cell lineage antigens (CD19, CD20, CD21, CD22, CD23, etc.), VEGFR, EGFR, carcinoembryonic antigen (CEA), placental growth factor (PLGF), tenascin, HER-2/neu, EGP-1, EGP-2, CD25, CD30, CD33, CD38, CD40, CD45, CD52, CD74, CD80, CD138, NCA66, CEACAM6

(carcinoembryonic antigen-related cellular adhesion molecule 6), MUC1, MUC2, MUC3, MUC4, MUC16, IL-6, α-fetoprotein (AFP), A3, CA125, colon-specific antigen-p (CSAp), folate receptor, HLA-DR, human chorionic gonadotropin (HCG), Ia, EL-2, insulin-like growth factor (ILGF) and ILGF receptor, KS-1, Le(y), MAGE, necrosis antigens, PAM-4, prostatic acid phosphatase (PAP), Prl, prostate specific antigen (PSA), prostate specific membrane antigen (PSMA), S100, T101, TAC, TAG72, TRAIL receptors, and carbonic anhydrase IX.

Targets associated with sepsis and immune dysregulation and other immune disorders include MIF, IL-1, IL-6, IL-8, CD74, CD83, and C5aR. Antibodies and inhibitors against C5aR have been found to improve survival in rodents with sepsis (Huber-Lang et al., *FASEB J* 2002; 16:1567-1574; Riedemann et al., *J Clin Invest* 2002; 110:101-108) and septic shock and adult respiratory distress syndrome in monkeys (Hangen et al., *J Surg Res* 1989; 46:195-199; Stevens et al., *J Clin Invest* 1986; 77:1812-1816). Thus, for sepsis, one of the at least two different targets preferably is a target that is associated with infection, such as LPS/C5a. Other preferred targets include HMGB-1, TF, CD14, VEGF, and IL-6, each of which is associated with septicemia or septic shock. Preferred multispecific antagonists are those that target two or more targets from HMGB-1, TF and MIF, such as MIF/TF, and HMGB-1/TF.

In still other embodiments, one of the at least two different targets may be a target this is associated with graft versus host disease or transplant rejection, such as MIF (Lo et al., *Bone Marrow Transplant*, 30(6):375-80 (2002)). One of the at least two different targets also may one that associated with acute respiratory distress syndrome, such as IL-8 (Bouros et al., *PMC Pulm Med*, 4(1):6 (2004), atherosclerosis or restenosis, such as MIF (Chen et al., *Arterioscler Thromb Vasc Biol*, 24(4):709-14 (2004), asthma, such as IL-18 (Hata et al., *Int Immunol*, Oct. 11, 2004 Epub ahead of print), a granulomatous disease, such as TNF-α (Ulbricht et al., *Arthritis Rheum*, 50(8):2717-8 (2004), a neuropathy, such as carbonylated EPO (erythropoietin) (Leist et al., *Science* 305(5681):164-5 (2004), or cachexia, such as IL-6 and TNF-α.

Other targets include C5a, LPS, IFN-gamma, B7; CD2, CD4, CD14, CD18, CD11a, CD11b, CD11c, CD14, CD18, CD27, CD29, CD38, CD40L, CD52, CD64, CD83, CD147, CD154. Activation of mononuclear cells by certain microbial antigens, including LPS, can be inhibited to some extent by antibodies to CD18, CD11b, or CD11c, which thus implicate β$_2$-integrins (Cuzzola et al., *J Immunol* 2000; 164:5871-5876; Medvedev et al., *J Immunol* 1998; 160: 4535-4542). CD83 has been found to play a role in giant cell arteritis (GCA), which is a systemic vasculitis that affects medium- and large-size arteries, predominately the extracranial branches of the aortic arch and of the aorta itself, resulting in vascular stenosis and subsequent tissue ischemia, and the severe complications of blindness, stroke and aortic arch syndrome (Weyand and Goronzy, *N Engl J Med* 2003; 349: 160-169; Hunder and Valente, In: Inflammatory Diseases of Blood Vessels. G. S. Hoffman and C. M. Weyand, eds, Marcel Dekker, New York, 2002; 255-265). Antibodies to CD83 were found to abrogate vasculitis in a SCID mouse model of human GCA (Ma-Krupa et al., *J Exp Med* 2004; 199:173-183), suggesting to these investigators that dendritic cells, which express CD83 when activated, are critical antigen-processing cells in GCA. In these studies, they used a mouse anti-CD83 Mab (IgG1 clone HB15e from Research Diagnostics). CD154, a member of the TNF family, is expressed on the surface of CD4-positive T-lymphocytes, and it has been reported that a humanized monoclonal antibody to CD154 produced significant clinical benefit in patients with active systemic lupus erythematosus (SLE) (Grammar et al., *J Clin Invest* 2003; 112:1506-1520). It also suggests that this antibody might be useful in other autoimmune diseases (Kelsoe, *J Clin Invest* 2003; 112:1480-1482). Indeed, this antibody was also reported as effective in patients with refractory immune thrombocytopenic purpura (Kuwana et al., *Blood* 2004; 103:1229-1236).

In rheumatoid arthritis, a recombinant interleukin-1 receptor antagonist, IL-1Ra or anakinra (Kineret®), has shown activity (Cohen et al., *Ann Rheum Dis* 2004; 63:1062-8; Cohen, *Rheum Dis Clin North Am* 2004; 30:365-80). An improvement in treatment of these patients, which hitherto required concomitant treatment with methotrexate, is to combine anakinra with one or more of the anti-proinflammatory effector cytokines or anti-proinflammatory effector chemokines (as listed above). Indeed, in a review of antibody therapy for rheumatoid arthritis, Taylor (*Curr Opin Pharmacol* 2003; 3:323-328) suggests that in addition to TNF, other antibodies to such cytokines as IL-1, IL-6, IL-8, IL-15, IL-17 and IL-18, are useful.

Some of the more preferred target combinations include the following:

| First target | Second target |
|---|---|
| MIF | A second proinflammatory effector cytokine, especially HMGB-1, TNF-α, IL-1, or IL-6 |
| MIF | Proinflammatory effector chemokine, especially MCP-1, RANTES, MIP-1A, or MIP-1B |
| MIF | Proinflammatory effector receptor, especially IL-6R IL-13R, and IL-15R |
| MIF | Coagulation factor, especially TF or thrombin |
| MIF | Complement factor, especially C3, C5, C3a, or C5a |
| MIF | Complement regulatory protein, especially CD46, CD55, CD59, and mCRP |
| MIF | Cancer associated antigen or receptor |
| HMGB-1 | A second proinflammatory effector cytokine, especially MIF, TNF-α, IL-1, or IL-6 |
| HMGB-1 | Proinflammatory effector chemokine, especially MCP-1, RANTES, MIP-1A, or MIP-1B |
| HMGB-1 | Proinflammatory effector receptor especially MCP-1, RANTES, MIP-1A, or MIP-1B |
| HMGB-1 | Coagulation factor, especially TF or thrombin |
| HMGB-1 | Complement factor, especially C3, C5, C3a, or C5a |
| HMGB-1 | Complement regulatory protein, especially CD46, CD55, CD59, and mCRP |
| HMGB-1 | Cancer associated antigen or receptor |
| TNF-α | A second proinflammatory effector cytokine, especially MIF, HMGB-1, TNF-α, IL-1, or IL-6 |
| TNF-α | Proinflammatory effector chemokine, especially MCP-1, RANTES, MIP-1A, or MIP-1B |
| TNF-α | Proinflammatory effector receptor, especially IL-6R IL-13R, and IL-15R |
| TNF-α | Coagulation factor, especially TF or thrombin |
| TNF-α | Complement factor, especially C3, C5, C3a, or C5a |
| TNF-α | Complement regulatory protein, especially CD46, CD55, CD59, and mCRP |
| TNF-α | Cancer associated antigen or receptor |
| LPS | Proinflammatory effector cytokine, especially MIF, HMGB-1, TNF-α, IL-1, or IL-6 |
| LPS | Proinflammatory effector chemokine, especially MCP-1, RANTES, MIP-1A, or MIP-1B |
| LPS | Proinflammatory effector receptor, especially IL-6R IL-13R, and IL-15R |
| LPS | Coagulation factor, especially TF or thrombin |

-continued

| First target | Second target |
|---|---|
| LPS | Complement factor, especially C3, C5, C3a, or C5a |
| LPS | Complement regulatory protein, especially CD46, CD55, CD59, and mCRP |
| TF or thrombin | Proinflammatory effector cytokine, especially MIF, HMGB-1, TNF-α, IL-1, or IL-6 |
| TF or thrombin | Proinflammatory effector chemokine, especially MCP-1, RANTES, MIP-1A, or MIP-1B |
| TF or thrombin | Proinflammatory effector receptor, especially IL-6R IL-13R, and IL-15R |
| TF or thrombin | Complement factor, especially C3, C5, C3a, or C5a |
| TF or thrombin | Complement regulatory protein, especially CD46, CD55, CD59, and mCRP |
| TF or thrombin | Cancer associated antigen or receptor |

In each of the above, the multispecific may include additional targets, e.g., third and further targets. This is a list of examples of preferred combinations, but is not intended to be exhaustive.

While the multispecific antagonist may be a mixture that contains at least two separate antibodies and/or receptors or their ligands that bind to the different targets, in one preferred embodiment the antagonist is an antibody that is at least bispecific, in which different arms of the antibody react specifically with at least two different targets, wherein the targets are selected from the group consisting of proinflammatory effectors of the innate immune system, coagulation factors, complement factors and complement regulatory proteins, and targets specifically associated with an inflammatory or immune-dysregulatory disorder, with a pathologic angiogenesis or cancer, or with an infectious disease.

There are certain advantages when the multispecific antagonist is an antibody that is at least bispecific, including rapid clearance from the blood. For example, the bispecific antibody may bind to a receptor or to its target molecule, such as for LPS, IL-1, IL-10, IL-6, MIF, HMGB1, TNF, IFN, tissue factor, thrombin, CD14, CD27, and CD134. Many of these exist as both receptors and as soluble forms in the blood. Binding by the bispecific antibodies results in rapid clearance from the blood, and then targeting by the second arm of the fusion protein to another cell, such as a macrophage, for transport and degradation by the cell, especially the lysosomes. This is particularly effective when the second targeting arm is against an internalizing antigen, such as CD74, expressed by macrophages and dendritic cells. This is consistent with the invention of Hansen, U.S. Pat. No. 6,458,933, but focusing herein on inflammatory cytokines and other immune modulation molecules and receptors for immune-dysregulation diseases, and cancer antigens for the immunotherapy of these cancers.

The multispecific antagonist may contain a single active component, or it may contain multiple active components. For example, when the multispecific antagonists comprise multiple separate antibodies, these constitute multiple active components. Alternatively, the multispecific antagonist may be a single active component, such as a multispecific antibody that reacts specifically with at least two different targets or a monospecific or multispecific antibody fused to a soluble receptor. The multispecific antagonist also may be packaged together with other secondary therapeutic modalities which are described below. The active components may be packaged together with one or more inactive components, such as a carrier or diluent, with instructions explaining the manner in which the components are to be combined. All components are conveniently packaged together in kit form with instructions regarding the combination and administration of the kit components. The components and agents may also be packaged and supplied separately.

Preferred multispecific antagonists for the treatment of cancer include antibodies to CD55 and to any of the above cancer antigens, antibodies to CD46 and to any of the above cancer antigens, antibodies to CD59 and to any of the above cancer antigens, antibodies to MIF and to any of the above cancer antigens, antibodies to NF-κB and any of the above cancer antigens, and antibodies to IL-6 and to any of the above cancer antigens other than IL-6. These multispecific antagonists for treating cancer may be antibody combinations or fusion proteins, given together or separately.

The multispecific antagonist may be used in conjunction with one or more secondary therapeutics. This secondary therapeutic may be one that affects a component of the innate immune system. Alternatively, it may affect a component of the adaptive immune system. The secondary therapeutic may also be a component that affects coagulation, cancer, or an autoimmune disease, such as a cytotoxic drug.

The multispecific antagonist with a diagnostic or therapeutic agent may be provided as a kit for human or mammalian therapeutic and diagnostic use in a pharmaceutically acceptable injection vehicle, preferably phosphate-buffered saline (PBS) at physiological pH and concentration. The preparation preferably will be sterile, especially if it is intended for use in humans. Optional components of such kits include stabilizers, buffers, labeling reagents, radioisotopes, paramagnetic compounds, second antibody for enhanced clearance, and conventional syringes, columns, vials and the like.

Production of Monoclonal Antibodies, Humanized Antibodies, Primate Antibodies and Human Antibodies Rodent monoclonal antibodies to available antigens can be obtained by methods known to those skilled in the art. See generally, for example, Kohler and Milstein, Nature 256:495 (1975), and Coligan et al. (eds.), CURRENT PROTOCOLS IN IMMUNOLOGY, VOL. 1, pages 2.5.1-2.6.7 (John Wiley & Sons 1991) ["Coligan"]. Briefly, monoclonal antibodies can be obtained by injecting mice with a composition comprising the antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen that was injected, culturing the clones that produce antibodies to the antigen, and isolating the antibodies from the hybridoma cultures.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS 1N MOLECULAR BIOLOGY, VOL. 10, pages 79-104 (The Humana Press, Inc. 1992).

Suitable amounts of well-characterized antigen for production of antibodies can be obtained using standard techniques. As an example, CD22 can be immunoprecipitated from B-lymphocyte protein using the deposited antibodies described by Tedder et al., U.S. Pat. No. 5,484,892 (1996). Alternatively, antigen proteins can be obtained from transfected cultured cells that overproduce the antigen of interest. Expression vectors that comprise DNA molecules encoding each of these proteins can be constructed using published nucleotide sequences. See, for example, Wilson et al, *J. Exp.*

*Med.* 173:137 (1991); Wilson et al, *J. Immunol.* 150:5013 (1993). DNA molecules encoding the antigen of interest can be obtained by synthesizing DNA molecules using mutually priming long oligonucleotides. See, for example, Ausubel et al., (eds.), CURRENT PROTOCOLS 1N MOLECULAR BIOLOGY, pages 8.2.8 to 8.2.13 (1990) ["Ausubel"]. Also, see Wosnick et al., *Gene* 60:115 (1987); and Ausubel et al. (eds.), SHORT PROTOCOLS 1N MOLECULAR BIOLOGY, 3rd Edition, pages 8-8 to 8-9 (John Wiley & Sons, Inc. 1995). Established techniques using the polymerase chain reaction provide the ability to synthesize genes as large as 1.8 kilobases in length. Adang et al, *Plant Molec. Biol.* 21:1131 (1993); Bambot et al., *PCR Methods and Applications* 2:266 (1993); Dillon et al., "Use of the Polymerase Chain Reaction for the Rapid Construction of Synthetic Genes," in METHODS 1N MOLECULAR BIOLOGY, Vol. 15: PCR PROTOCOLS: CURRENT METHODS AND APPLICATIONS, White (ed.), pages 263-268, (Humana Press, Inc. 1993).

In an alternative embodiment, an antibody of the present invention is a chimeric antibody in which the variable regions of a human antibody have been replaced by the variable regions of a rodent antibody. The advantages of chimeric antibodies include decreased immunogenicity and increased in vivo stability.

Techniques for constructing chimeric antibodies are well known to those of skill in the art. As an example, Leung et al., *Hybridoma* 13:469 (1994), describe how they produced an LL2 chimera by combining DNA sequences encoding the $V_\kappa$ and $V_H$ domains of LL2 monoclonal antibody with respective human κ and $IgG_1$ constant region domains. This publication also provides the nucleotide sequences of the LL2 light and heavy chain variable regions, $V_\kappa$ and $V_H$, respectively.

In another embodiment, an antibody of the present invention is a subhuman primate antibody. General techniques for raising therapeutically useful antibodies in baboons may be found, for example, in Goldenberg et al., international patent publication No. WO 91/11465 (1991), and in Losman et al., *Int J Cancer* 46: 310 (1990).

In yet another embodiment, an antibody of the present invention is a "humanized" monoclonal antibody. That is, mouse complementarity determining regions (CDRs) are transferred from heavy and light variable chains of the mouse immunoglobulin into a human variable domain, followed by the replacement of some human residues in the framework regions of their murine counterparts. Humanized monoclonal antibodies in accordance with this invention are suitable for use in therapeutic methods. General techniques for cloning murine immunoglobulin variable domains are described, for example, by the publication of Orlandi et al., *Proc Nat'l Acad Sci USA* 86:3833 (1989). Techniques for producing humanized monoclonal antibodies are described, for example, by Jones et al., *Nature* 321:522 (1986), Riechmann et al., *Nature* 332:323 (1988), Verhoeyen et al., *Science* 239:1534 (1988), Carter et al., *Proc. Nat'l Acad. Sci. USA* 89:4285 (1992), Sandhu, Crit. Rev Biotech. 12:437 (1992), and Singer et al., *J Immun* 150:2844 (1993). The publication of Leung et al., *Mol Immunol* 32:1413 (1995), describes the construction of humanized LL2 antibody.

In another embodiment, an antibody of the present invention is a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet* 7:13 (1994), Lonberg et al., *Nature* 368:856 (1994), and Taylor et al., *Int Immun* 6:579 (1994).

A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g., Johnson and Chiswell, *Current Opinion in Structural Biology,* 3:5564-571 (1993).

Although xenogeneic antibodies may be used in the invention, it is preferable to use allogeneic antibodies to reduce the likelihood of the antibodies themselves inducing an immune response from the host. In a particular embodiment of the invention, a human antibody is used. Methods for making fully human antibodies for use in human subjects include the use of phage display techniques for selecting antigen specific antibodies from a large human antibody library, as described in U.S. Pat. No. 5,969,108, which is incorporated herein by reference in its entirety. Other phage display methods for making human antibodies from designed human antibody libraries are described in U.S. Pat. No. 6,300,064, which is incorporated herein by reference in its entirety. See also: Marks, et al. "By-Passing Immunization: Building High Affinity Human Antibodies by Chain Shuffling." (Bio/Technology, vol. 10: p. 779-783. (1992)), Hoogenboom, et al. "Building Antibodies From Their Genes." (*Rev Fr Transfus Hemobiol,* vol. 36: p. 19-47, (1993)); Griffiths, et al. "Isolation of High Affinity Human Antibodies Directly from Large Synthetic Repertoires." *EMBO J,* vol. 13: p. 3245-3260 (1994)); Winter and Milstein "Man-Made Antibodies." (*Nature,* vol. 349: p. 293-299 (1991)); De Kruif, et al., "Selection and Application of Human Single Chain Fv Antibody Fragments from a Semi-synthetic Phage Antibody Display Library with Designed CDR3 Regions," (*J Mol Biol,* vol. 248, pp. 97-105 (1995)) and Barbas et al., "Semisynthetic combinatorial antibody libraries: A chemical solution to the diversity problem," (*Proc Natl Acad. Sci. USA,* vol. 89, pp. 4457-4461 (1992)). Other methods for making fully human antibodies include the use of so-called "xenomouse" technology, using transgenic mice that encode a large portion of the human antibody repertoire. These methods are provided commercially by, for example, Abgenix (Fremont Calif.) and Medarex (Princeton N.J.). See also, U.S. Pat. No. 6,075,181; Lonberg, "Transgenic Approaches to Human Monoclonal Antibodies." *Handbook of Experimental Pharmacology* 113 (1994): 49-101; Lonberg et al.,. "Human Antibodies from Transgenic Mice."*Internal Review of Immunology* 13 (1995): 65-93.

Production of Multispecific Antibodies

The multispecific antagonists according to the present invention may be multispecific antibodies or antibody fragments, particularly bispecific antibodies (bsAb) or bispecific antibody fragments (bsFab). These multispecific antagonists have arms that specifically bind to at least two different targets, where the targets are selected from the group consisting of proinflammatory effectors of the innate immune system, coagulation factors, and targets specifically associated with an inflammatory or immune-dysregulatory disorder or with a pathologic angiogenesis, where the latter target is not a proinflammatory effector of the immune system, a coagulation factor or a cancer cell receptor or cancer-associated antigen.

The present invention may employ a pretargeting strategy, in which one arm of a multispecific antibody or fragment binds to a targetable conjugate. Pretargeting strategies based on avidin or streptavidin and biotin may be used, as described in Goldenberg, U.S. Pat. No. 5,525,338, entitled "Detection and Therapy of Lesions with Biotin/Avidin Conjugates." The avidin/streptavidin system is highly versatile and has been used in several configurations. Antibodies can be coupled with streptavidin or biotin, which is used as the primary targeting agent. This is followed sometime later by the therapeutic agent, which is conjugated with biotin or with avidin/streptavidin, respectively. Another configuration relies on a 3-step approach first targeting a biotin-conjugated antibody, followed by a bridging with streptavidin/avidin, and then the biotin-conjugated therapeutic agent is given. Description of biotin and avidin/streptavidin conjugation to antibodies and other species is well-known in the art. See, for example, Griffiths et al., U.S. Pat. No. 5,846,741; Griffiths et al, U.S. Pat. No. 5,965,115, and Griffiths et al., U.S. Pat. No. 6,120,768. While the avidin-biotin system has a very high affinity, clinical experience has shown that approximately 20-30% of patients mount an antibody response against avidin and up to 70% make antibodies to streptavidin. Accordingly, low-molecular weight haptens are more preferred.

In this embodiment, the multispecific antagonist is a multispecific antibody that comprises an arm that is specific for a low-molecular weight hapten to which a therapeutic agent is conjugated or fused. In this case, the antibody pretargets the cells, and the low-molecular weight hapten with the attached therapeutic agent is administered after the antibody has bound to the targets. Examples of recognizable haptens include, but are not limited to, chelators, such as DTPA, DOTA, fluorescein isothiocyanate, vitamin B-12 and other moieties to which specific antibodies can be raised. The subsequently injected haptens can carry different diagnostic or therapeutic agents. More than one multispecific antibody also may be used, each of which comprises an arm which recognizes the same hapten. The use of multispecific antibodies, and combinations of multispecific antibodies, is particularly effective in overcoming antigen heterogeneity in tumors and other diseased tissue.

The use of hapten-therapy agent conjugates for the localization of therapeutics to disease targets has several distinct advantages. The same hapten can be attached to several different therapy agents. In addition, should an immune response to one therapy agent be seen, this will not destroy the ability of a developed non-immunogenic antibody targeting vector to be used in hapten-therapy agent-based systems. This also enables the use of a universal targeting system that can be used with any targeting antibody and therapy agent combination. In using a hapten recognition system the designing chemist has control over how haptens are attached to a therapy agent, and is able to incorporate features such as liability to a particular extra-cellular or intracellular enzyme, or instability to a particular set of conditions, such as slightly lowered pH.

The carrier portion is conjugated to a proinflammatory effector of the innate immune system, a coagulation factor, or a target specifically associated with an inflammatory or immune-dysregulatory disorder or with a pathologic angiogenesis that is neither a proinflammatory effector of the innate immune system or a coagulation factor. The use of multispecific antibodies and fragments which have at least one arm that specifically binds a targetable conjugate allows a variety of therapeutic applications to be performed without raising new multispecific antibody for each application.

MAbs can be raised to any hapten or drug by standard methods of making mAbs known to a person skilled in the art. For instance, it is possible to attach, a hapten such as HSG (histamine-succinyl-glycine) to an immunogenic stimulator or adjuvant such a keyhole limpet hemocyanin, and inject the conjugate into immunocompetent animals. Multiple injections are often employed. It must be appreciated that such an approach can lead to several different antibodies with slightly different specificities against the hapten in question, such as HSG. MAbs can recognize different sub-parts of the HSG structure, or different conformations. MAbs may also be obtained that recognize a little more than just the HSG molecule itself, such as recognizing an HSG moiety only when attached to an epsilon amino group of lysine, if indeed, the HSG was initially linked to the KLH (for example) by attachment to an epsilon lysyl amino group on the latter immunogenic protein. Without wishing to be exhaustive, these general procedures and results are well known in the art. It is also then well known art for the isolation of spleen cells producing antibodies from these immunized animals, and their subsequent fusion with myeloma cell lines, to generate hybridomas secreting anti-hapten antibodies. See Kohler G. and Milstein C., *Eur J Immunol* 6:511-9 (1976); Kohler G. et al, *Eur J Immunol* 6:292-5 (1976); and Kohler G. and Milstein C. *Nature* 256:495-7 (1975).

Multispecific targeting proteins can be prepared chemically from antibodies that have differing specificity by well-known reactions. Typically, one MAb is activated by reaction with a cross-linking agent, with the latter chosen to react at the first MAb's lysine, reduced cysteine, or oxidized carbohydrate residues. After purification, the activated first MAb is mixed with the second MAb, which then reacts specifically with a second functionality of the original cross-linking agent; most notably via the second MAb's lysine, reduced cysteine or oxidized carbohydrate residues. Multispecific targeting proteins can also be prepared somatically by the quadroma technique. The quadroma technique is a technique wherein a cell line expressing both arms of the bispecific antibody is produced and grown in culture to secrete the bsMAb. Finally, bsMAbs can also be produced conveniently by modem techniques of molecular biology. See, for example, Colman, A., *Biochem Soc Symp* 63: 141-147 (1998); U.S. Pat. No. 5,827,690; and Published U.S. Application 20020006379.

The present invention encompasses antibodies and antibody fragments. Antibodies are generally bivalent, or less often multivalent, and this bivalency enhances the strength of attachment of the antibody to cell surfaces. However, the bivalency of the antibody sometimes induces a target cell to undergo antigenic modulation thereby providing a means whereby the cell can avoid the cytotoxic agents, effector cells and complement, which are involved in the cell-antibody interaction. As a means of preventing such modulation, monovalent antibodies or antibody fragments can be used. A monovalent antibody is a complete, functional immunoglobulin molecule in which only one of the light chains binds to antigen. One method of preparing such antibodies is disclosed in U.S. Pat. No. 4,841,025.

Monovalency can be achieved by using antibody fragments. Exemplary monovalent antibody fragments useful in these embodiments are Fv, Fab, Fab' and the like. Monovalent antibody fragments, typically exhibiting a molecular weight ranging from about 25 kD (Fv) to about 50 kD (Fab, Fab'), are smaller than whole antibody and, therefore, are generally capable of greater target site penetration. Moreover, monovalent binding can result in less binding carrier restriction at the target surface (occurring during use of bivalent antibodies, which bind strongly and adhere to target cell sites thereby creating a barrier to further egress into sublayers of target tissue), thereby improving the homogeneity of targeting. In addition, smaller molecules are more rapidly cleared from a recipient, thereby decreasing the immunogenicity of the administered small molecule conjugate. A lower percentage of the administered dose of a monovalent fragment conjugate localizes to target in comparison to a whole antibody conjugate. The decreased immunogenicity may permit a greater initial dose of the monovalent fragment conjugate to be administered, however. In addition, monovalent antibody fragments generally do not reside as long on the target cell as do bivalent or whole antibodies.

The antibody fragments are antigen binding portions of an antibody, such as F(ab')2, F(ab)$_2$, Fab', Fab, and the like. The antibody fragments bind to the same antigen that is recognized by the intact antibody. For example, an anti-CD22 monoclonal antibody fragment binds to an epitope of CD22. The bsAb of the present invention include, but are not limited to, IgG×IgG, IgG×F(ab'), IgG×Fab', IgG×scFv, F(ab')$_2$×F(ab')$_2$, Fab'×F(ab')$_2$, Fab'×Fab', Fab'×scFv and scFv×scFv bsMabs. Also, species such as scFv×IgG×scFv and Fab'×IgG×Fab', scFv×F(ab')$_2$×scFv and Fab'×F(ab')2×Fab' are included.

As noted above, the term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("sFv proteins"), and minimal recognition units consisting of the amino acid residues that mimic the hypervariable region.

Production of Fusion Proteins

Another method for producing multispecific antagonists is to engineer recombinant fusion proteins linking two or more different single-chain antibody or antibody fragment segments with the needed multiple specificities. See, e.g., Coloma et al., *Nature Biotech* 15:159-163, 1997. For example, a variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

Functional bispecific single-chain antibodies (bscAb), also called diabodies, can be produced in mammalian cells using recombinant methods. See, e.g., Mack et al., *Proc Natl Acad Sci*, 92:7021-7025, 1995. For example, bscAb are produced by joining two single-chain Fv fragments via a glycine-serine linker using recombinant methods. The V light-chain (V$_L$) and V heavychain (V$_H$) domains of two antibodies of interest are isolated using standard PCR methods. The V$_L$ and V$_H$ cDNA's obtained from each hybridoma are then joined to form a single-chain fragment in a two-step fusion PCR. The first PCR step introduces the (Gly4-Ser1)$_3$ linker, and the second step joins the V$_L$ and V$_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into a eukaryotic expression vector. Functional protein expression can be obtained by transfecting the vector into Chinese hamster ovary cells. Recombinant methods can be used to produce a variety of fusion proteins.

Production of Immunoconjugates

Any of the multispecific antagonists of the present invention can be conjugated with one or more therapeutic or diagnostic/detection agents. Generally, one therapeutic or diagnostic/detection agent is attached to each antibody, fusion protein or fragment thereof but more than one therapeutic agent and/or diagnostic/detection agent can be attached to the same antibody or antibody fragment. If the Fc region is absent (for example when the antibody used as the antibody component of the immunoconjugate is an antibody fragment), it is possible to introduce a carbohydrate moiety into the light chain variable region of a full length antibody or antibody fragment. See, for example, Leung et al., *J Immunol* 154: 5919 (1995); Hansen et al., U.S. Pat. No. 5,443,953 (1995), Leung et al., U.S. Pat. No. 6,254,868. The engineered carbohydrate moiety is used to attach the therapeutic or diagnostic/detection agent.

Methods for conjugating peptides to antibody components via an antibody carbohydrate moiety are well-known to those of skill in the art. See, for example, Shih et al., *Int Cancer* 41: 832 (1988); Shih et al., *Int J Cancer* 46: 1101 (1990); and Shih et al., U.S. Pat. No. 5,057,313. The general method involves reaction of an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

A therapeutic or diagnostic/detection agent can be attached at the hinge region of a reduced antibody component via disulfide bond formation. As an alternative, such agents can be attached to the antibody component using a heterobifunctional cross-linker, such as N-succinyl 3-(2-pyridyldithio) proprionate (SPDP). Yu et al., *Int J Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic/detection agent can be conjugated via a carbohydrate moiety in the Fc region of the antibody. The carbohydrate group can be used to increase the loading of the same agent that is bound to a thiol group, or the carbohydrate moiety can be used to bind a different peptide.

Coupling of Antibodies to Lipid Emulsions

Long-circulating sub-micron lipid emulsions, stabilized with poly(ethylene glycol)-modified phosphatidylethanolamine (PEG-PE), can be used as drug carriers for the antibodies of the present invention. The emulsions are composed of two major parts: an oil core, e.g., triglyceride, stabilized by emulsifiers, e.g., phospholipids. The poor emulsifying properties of phospholipids can be enhanced by adding a biocompatible co-emulsifier such as polysorbate 80. In a preferred embodiment, the antibody is conjugated to the surface of the lipid emulsion globules with a poly(ethylene glycol)-based, heterobifunctional coupling agent, poly(ethylene glycol)vinylsulfone-N-hydroxy-succinimidyl ester (NHS-PEG-VS).

The submicron lipid emulsion is prepared and characterized as described. Lundberg, *J Pharm Sci*, 83:72 (1993); Lundberg et al., *Int J Pharm*, 134:119 (1996). The basic composition of the lipid emulsion is triolein:DPPC:polysorbate 80, 2:1:0.4 (w/w). When indicated, PEG-DPPE is added into the lipid mixture at an amount of 2-8 mol % calculated on DPPC.

The coupling procedure starts with the reaction of the NHS ester group of NHS-PEG-VS with the amino group of distearoyl phosphatidyl-ethanolamine (DSPE). Twenty-five μmol of NHS-PEG-VS are reacted with 23 μmol of DSPE and 50 μmol triethylamine in 1 ml of chloroform for 6 hours at 40° C. to produce a poly(ethylene glycol) derivative of phosphatidyl-ethanolamine with a vinylsulfone group at the distal terminus of the poly(ethylene glycol) chain (DSPE-PEG-VS). For antibody conjugation, DSPE-PEG-VS is included in the lipid emulsion at 2 mol % of DPPC. The components are dispersed into vials from stock solutions at −20° C., the solvent is evaporated to dryness under reduced pressure. Phosphate-buffered saline (PBS) is added, the mixture is heated to 50° C., vortexed for 30 seconds and sonicated with a MSE probe sonicator for 1 minute. Emulsions can be stored at 4° C., and preferably are used for conjugation within 24 hours.

Coupling of antibodies to emulsion globules is performed via a reaction between the vinylsulfone group at the distal PEG terminus on the surface of the globules and free thiol groups on the antibody. Vinylsulfone is an attractive derivative for selective coupling to thiol groups. At approximately neutral pH, VS will couple with a half life of 15-20 minutes to proteins containing thiol groups. The reactivity of VS is slightly less than that of maleimide, but the VS group is more stable in water and a stable linkage is produced from reaction with thiol groups.

Before conjugation, the antibody is reduced by 50 mM 2-mercaptoethanol for 10 minutes at 4° C. in 0.2 M Tris buffer (pH 8.7). The reduced antibody is separated from excess 2-mercaptoethanol with a Sephadex G-25 spin column, equilibrated in 50 mM sodium acetate buffered 0.9% saline (pH 5.3). The product is assayed for protein concentration by measuring its absorbance at 280 nm (and assuming that a 1 mg/ml antibody solution of 1.4) or by quantitation of $^{125}$I-labeled antibody. Thiol groups are determined with Aldrithiol® following the change in absorbance at 343 nm and with cysteine as standard.

The coupling reaction is performed in HEPES-buffered saline (pH 7.4) overnight at ambient temperature under argon. Excess vinylsulfone groups are quenched with 2 mM 2-mercaptoethanol for 30 minutes, excess 2-mercaptoethanol and antibody are removed by gel chromatography on a Sepharose CL48 column. The immunoconjugates are collected near the void volume of the column, sterilized by passage through a 0.45 μm sterile filter, and stored at 4° C.

Coupling efficiency is calculated using $^{125}$I-labeled antibody. Recovery of emulsions is estimated from measurements of [$^{14}$C]DPPC in parallel experiments. The conjugation of reduced LL2 to the VS group of surface-grafted DSPE-PEG-VS is very reproducible with a typical efficiency of near 85%.

Therapeutic Use of Multispecific Antagonists in Single and Multimodal Regimens

The present invention relates to the therapy of diverse acute and chronic inflammatory and immune-dysregulatory diseases, as well as certain cancers, by having specific antibodies and antibody heteroconjugates for binding to various host cells participating in immune responses of the innate or adaptive (acquired) immune system and by modulating the actions of critical cells and receptors by agonistic or antagonistic actions. Of particular advantage is the use of bi- and multifunctional (bispecific or multispecific) antibodies targeting these cells/receptors as well as target molecules of the diseased cells/tissues. See Hansen, U.S. Pat. No. 6,458,933, incorporated herein by reference in its entirety. Whereas Hansen focuses on clearing the host of the pathogen (infectious organisms and cancers), the therapeutic or diagnostic agents, autoantibodies, or anti-graft antibodies, the present invention enables the alteration of host immunity against certain diseases by targeting the appropriate host cells involved in immunity and the target cells/receptors expressed by the diseased cells.

The multispecific antagonists are formulated according to known methods to prepare pharmaceutically useful compositions, in which the therapeutic proteins are contained in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, REMINGTON'S PHARMACEUTICAL SCIENCES, 19th Ed. (1995), and later editions.

For purposes of therapy, the multispecific antagonists are administered, alone or conjugated to liposomes, to a patient in a therapeutically effective amount in a pharmaceutically acceptable carrier. In this regard, a "therapeutically effective amount" is one that is physiologically significant. An agent is physiologically significant if its presence results in a detectable change in the physiology of a recipient patient. In the present context, an agent is physiologically significant if its presence results in the inactivation or killing of targeted cells.

When therapy with naked multispecific antagonists is used, it merely entails administering the antagonist to a subject in need of such treatment, and allowing sufficient time for the antagonist to bind to its targets. When therapy involves a multi specific antagonist that includes a hapten binding site, the subject is first administered the multispecific antagonist and then, after waiting a sufficient amount of time for the antagonist to localize and for unbound antagonist to clear the subject's blood stream, a carrier molecule that comprises a therapeutic agent is administered to the subject that binds to the hapten binding site on the multispecific antagonist. Alternatively, clearing agent may be administered after allowing the antagonist to bind to the target. Such pretargeting methods are described in detail, for example, in Gautherot et al., *Cancer*, 80 (12 Suppl):2618-23 (1997); Karacay et al., *Bioconjug Chem*, 11:842-54 (2000); Sharkey et al., *Cancer Res*, 63:354-63 (2003); Sharkey et al., *Clin Can Res*, 9(10 Pt 2):3897S-913S; and US Patent Appln. Serial nos. 20030232011A1 and 20040241158A1. If a secondary therapeutic forms part of the therapeutic regimen, it can be administered prior to, concurrently with, or after the multispecific antagonist is administered.

The multispecific antagonists described herein are useful for treatment of autoimmune diseases, particularly for the treatment of Class III autoimmune diseases including immune-mediated thrombocytopenias, such as acute idiopathic thrombocytopenic purpura and chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiform, IgA nephropathy, polyarteritis nodosa, ankylosing spondylitis, Goodpasture's syndrome, thromboangiitis ubiterans, Sjogren's syndrome, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

The multispecific antagonists also are useful in treating inflammatory or immune-dysregulatory disorders other than autoimmune disease. Examples of these other inflammatory or immune-dysregulatory disorders that can be treated with composition according to the invention include septicemia or septic shock, infection, neuropathies, graft versus host disease, transplant rejection, acute respiratory distress syndrome, granulomatous disease, asthma, acne, diffuse intravascular coagulation (DIC), and atherosclerosis.

In addition to their use in treating inflammatory and immune-dysregulatory disorders, including autoimmune diseases, the therapeutic compositions also are useful for treating a pathologic angiogenesis and cancer. Cancer includes both hematopoietic cancers, such as leukemias, lymphomas, and myelomas, and solid cancers, such as carcinomas, melanomas, gliomas, etc. Leukemias include the myelocytic leukemias, such as AML and CML, lymphatic leukemias, such as ALL and CLL, and T-cell leukemias. Lymphomas include non-Hodgkin's lymphoma, Hodgkin's lymphoma, and T-cell lymphomas. The therapeutic compositions also are useful in treating the cachexia that may accompany cancer, infections, and some autoimnuune diseases. In particular, multispecific antagonists according to the invention preferably include IL-6 or TNF-α as a target in this embodiment.

The multispecific antagonists also can be used in treating inflammation associated with an infectious disease, including viral infections, bacterial infections, parasitic infections, and fungal infections. Exemplary viruses include the species of human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus. Exemplary bacteria include Anthrax bacillus, Streptococcus agalactiae, Legionella pneumophilia, Streptococcus pyogenes, Escherichia coli, Neisseria gonorrhoeae, Neisseria meningitidis, Pneumococcus, Hemophilis influenzae B, Treponema pallidum, Lyme disease spirochetes, Pseudomonas aeruginosa, Mycobacterium leprae, Brucella abortus, Mycobacterium tuberculosis and Tetanus toxin. Exemplary protozoans are Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileriaparva, Taenia hydatigena, Taenia ovis, Taenia saginata, Echinococcus granulosus or Mesocestoides corti. Exemplary mycoplasmas are Mycoplasma arthritidis, Mycoplasma hyorhinis, Mycoplasma orale, Mycoplasma arginini, Acholeplasma laidlawii, Mycoplasma salivarum, and Mycoplasma pneumoniae. The fungus may be from the species of Microsporum, Trichophyton, Epidermophyton, Ssporothrix schenckii, Cyrptococcus neoformans, Coccidioides immitis, Histoplasma capsulatum, Blastomyces dermatitidis, or Candida albicans. Exemplary fungi include the species of Microsporum, Trichophyton, Epidermophyton, Ssporothrix schenckii, Cyrptococcus neoformans, Coccidioides immitis, Histoplasma capsulatum, Blastomyces dermatitidis, or Candida albicans. Exemplary parasites include malarial parasites, spirochetes and the like, including helminthes. Listings of representative disease-causing infectious organisms to which antibodies can be developed for use in this invention are contained in the second and subsequent editions of Davis et al., MICROBIOLOGY (Harper & Row, New York, 1973 and later), and are well known to one of ordinary skill in the art. In these embodiments, the multispecific antibody preferably targets an antigen associated with the microbe or parasite.

Sepsis and septic shock are characterized by overwhelming inflammatory and immune responses, which make them particularly susceptible to treatment with multispecific antagonists according to the present invention. Treatment of these conditions according to the present invention entails combining agents that work via different mechanisms, and preferably by administering fusion proteins of antagonist or agonist mediators or antibodies which function against more than one target molecule involved in the pathogenesis of this immune dysregulatory, inflammatory disease. As advocated by Van Amersfoort et al. (ibid.), "an attempt should be made to restore the balance between the pro- and anti-inflammatory responses." The present invention restores the balance and provides a clear improvement art over the use of single agents that neutralize the proinflammatory cytokines such TNF or IL-1 in patients with sepsis, by using multispecific antagonists specific for at least two different targets, where the targets are selected from the group consisting of proinflammatory effectors of the innate immune system, coagulation factors, and targets specifically associated with sepsis or septic shock.

In one embodiment for treatment of sepsis or septic shock, different anti-inflammatory agents are combined with activated protein C, as well as with anti-coagulation agents, and at least one component of this multiple agent therapy is an agonist or antagonist antibody to at least one target receptor or mediator of inflammation or coagulation, including complement pathway antagonists. A listing of selected anti-inflammatory and immunomodulating agents used to treat patients with severe sepsis and septic shock is found in Bochud and Calandra (*Brit Med J* 2003; 326:262-266), and clinical trials of most of these immunomodulatory therapies of severe sepsis and septic shock are reviewed in Vincent et al., *Clin Infect Dis* 2002; 34:1084-93.

Particularly preferred agents useful in treatment of sepsis and septic shock are multispecific antagonists that target MIF, LPS, TNF-α, C5a receptor (C5aR), TLR2 or HMGB-1 as one of the targets. The other target can also be selected from these, as well as from other proinflammatory cytokines or receptors, such as interleukin IL-1, TSST-1 (toxic shock syndrome toxin 1), NCA-90, NCA-95, and HLA-DR. Preferred combinations of agents or fusion proteins for treatment of severe sepsis or septic shock include those that target MIF and C5a receptor (C5aR), MIF and IL-6, LPS and MIF, TNF-α and HMGB-1, TLR2 (toll-like receptor-2) and LPS, TLR2 and IL-6, TLR2 and C5aR. An anti-MIF/anti-NCA-90 or an anti-MIF/anti-HLA-DR multispecific antagonist can be used to target granulocytes in blood/infectious deposits to neutralize MIF in patients with early evidence of toxic shock. Preferably these are humanized or human antibody constructs. These are readily combined or constructed by those of skill in the art from available antibodies. For example, T2.5 Mab has been developed as an antagonist to TLR-2 by immunizing a TLR2-neg mouse with TLR2 extracellular domain, and this antibody inhibits release of inflammatory mediators, such as TNF-α and prevents lethal shock-like syndrome in mice (Meng et al., *J Clin Invest* 2004; 113:1473-1481). In preferred embodiments, recombinant activated protein C is used as a secondary therapeutic in combination with antibody mixtures and fusion proteins.

It also has been discovered according to the invention that the multispecific antagonists which target both a complement regulatory factors such as CD46, CD55, and/or CD59 and a tumor-associated antigen, and more particularly at least bispecific antibodies in which one arm targets the complement regulatory factor and a second arm targets an tumor associated antigen, are more effective in treating cancer than antibodies that target just one of these antigens. Moreover, contrary to the teaching of Sier et al., supra, it has been discovered that the use of beta-glucan is not obligatory in vivo for the improved efficacy of a such a multispecific antagonist over the use of the anticancer antibody alone, and that the bispecific antibody targeting the cancer and the complement-regulatory protein (e.g., CD55) increases cancer cell killing over either antibody used by itself, specifically against tumors that have a high expression of the complement-regulatory protein (thus blocking complement-mediated cytotoxicity by antibodies).

Another preferred complement-related target for neutralizing antibodies is complement factor H (and its variant FHL-1) involved in the alternative pathway for complement, especially since factor H may be overexpressed by some cancers (Ajona et al., *Cancer Res* 2004; 64:6310-6318, and references cited therein). Therefore, use of multispecific antagonists, and particularly multispecific antibodies, directed against complement factor H and factor FHL-1 are of particular importance. Multispecific antagonists against complement factor H and its variant FHL-1 additionally may target CD55, CD46 and/or CD59, as well as other complement factors. The targeting of these multispecific antagonists and to tumor-associated antigens and receptors has been found to enhance specific targeting of complement antibodies to the tumor cells, and to provide an advantage over use of antibodies targeting a single antigen or epitope. This has overcome the inconsistencies in the literature published to date.

In non-malignant conditions, there is a different approach. This includes neutralization or interference with other complement receptors or factors, including complement-derived anaphylatoxin C5a or complement-receptor 3 (CR3, CD18/11b), which can mediate adhesion of inflammatory cells to the vascular endothelium. In such situations, increased expression of CD46, CD55, and/or CD59 is desired in order to mitigate complement-mediated immunity, and also to reduce hyperacute rejection, as in organ transplant-rejection. Therefore, use of agonists of such complement regulatory factors would be advantageous.

Particularly preferred agents useful in treatment of atherosclerosis are multispecific antagonists that target MIF, low-density lipoprotein (LDL), and CEACAM6 (e.g., NCA-90). The other target can also be selected from these, as well as from other proinflammatory cytokines. Preferred combinations of agents or fusion proteins for treatment of atherosclerosis target MIF and low-density lipoprotein-modified epitopes, NCA-90 and MIF, NCA-90 and low-density lipoprotein (LDL) epitopes, or LDL and CD83. There are readily combined or constructed by those of skill in the art from commercially available antibodies. For example, Mab MDA2, a prototype Mab, recognizes malondialdehyde-lysing epitopes (e.g., in malondialdehyde-modified LDL) within oxidation-rich atherosclerotic lesions (as described by Tsimikas et al., *J Nucl Cardiol* 1999; 6:81-90).

In addition to sepsis and atherosclerosis, MIF has been reported to be expressed in rabbits with atherogenesis (Lin et al., *Circulation Res* 2000; 87:1202-1208), indicating that it is a key cytokine for this condition. Other diseases in which MIF has been implicated include glomerulonephritis, arthritis, delayed-type hypersensitivity, gastric inflammation, and acute myocardial ischemia (reviewed by Yu et al., *J Histochem Cytochem* 2003; 625-631). Multispecific antagonists that target MIF are therefore useful in treating any of these conditions.

As many as 500,000 individuals in the U.S. develop sepsis each year, a number that is rising with the aging of the population. Despite the best in antibiotic therapy and cardiopulmonary support, and the advances in understanding of inflammation and coagulation in sepsis, as many as half these cases are fatal. During infection, pro-inflammatory cytokines are released and activated. These include TNF-α, IL-1, and IL-6. Anti-inflammatory mediators, including IL4 and IL-10, appear insufficient to regulate pro-inflammatory cytokines in severe sepsis.

Prominent features of the septic response include uncontrolled inflammation and coagulation. Vascular endothelial damage is the triggering event, whether caused by endotoxin, tissue factor, necrotic cells, or amniotic fluid, becomes the triggering event. This endothelial damage leads to release of tissue factor, which activates the coagulation system resulting in excess thrombin generation. Subsequent clot formation promotes microvascular endothelial dysfunction, and, if unchecked, hypoxemic, organ dysfunction, and organ failure ensue.

Endothelial damage and a shift towards a prothrombotic milieu lead to decreased expression and impaired function of endothelial receptors for thrombin, i.e., thrombomodulin, and protein C, i.e., the endothelial protein C receptor (EPCR). Both thrombomodulin and EPCR are required for the conversion of protein C to its active form, APC. Thus, a major system for the regulation of thrombin formation, clot propagation, and protein C activation is lost.

Nearly all patients with severe sepsis are deficient in protein C. Low protein C levels are associated with shock and poor outcomes, including ICU stay, ventilator dependence, and mortality. Supplying activated protein C exogenously in severe sepsis helps to restore regulation of inflammatory and coagulation responses in some patients, leading to a favorable survival benefit. However, there is an obvious need for new therapeutic modalities to reduce the procoagulant response, and prevent septic organ injury.

It has been established that blocking initiation of the procoagulant response before sepsis decreases mortality in non-human primates. Effective strategies to block initiation of extrinsic coagulation have included use of monoclonal antibodies to TF, the natural TF pathway inhibitor, and inactive analogs of FVIIa. In a recent study in baboons, it was demonstrated that blockade of the TF-VIIa complex with FVIIai at the onset of sepsis attenuated sepsis-induced multiple organ injury and dramatically protected the lungs and kidneys. Antagonists that inhibit complement activation products, especially the anaphylatoxins, also offer promise to decrease sepsis mortality. C3a, C4a and C5a, appear during sepsis, and the elevated anaphylotoxin plasma levels highly correlate with the development of multiorgan failure. In sepsis, complement may directly promote procoagulant activity or indirectly induce cytokine production. In vitro C5a and the terminal complex of complement, C5b-9, induce tissue factor expression on endothelial cells and monocytes, and assembly of C5b-9 on the surface of platelets has been shown to stimulate prothrombinase activity. The present invention provides improved therapeutics for treating sepsis by providing multispecific antagonists that target two or more of coagulation factors, proinflammatory cytokines and complement activations products.

Additional pharmaceutical methods may be employed to control the duration of action of an antibody in a therapeutic application. Control release preparations can be prepared through the use of polymers to complex or adsorb the antibody. For example, biocompatible polymers include matrices of poly(ethylene-co-vinyl acetate) and matrices of a polyanhydride copolymer of a stearic acid dimer and sebacic acid. Sherwood et al., *Bio/technology* 10:1446 (1992). The rate of release of an antibody from such a matrix depends upon the molecular weight of the protein, the amount of antibody within the matrix, and the size of dispersed particles. Saltzman et al., *Biophys J* 55:163 (1989); Sherwood et al., supra. Other solid dosage forms are described in REMINGTON'S PHARMACEUTICAL SCIENCES, 19th ed. (1995).

The multispecific antagonists according to the invention bind to various immune or other host cells involved in the generation of inflammation and other immune-dysregulatory diseases (including intravascular coagulation and myocardial ischemia). They also can be used to enhance a host's immune response to cancer for cancer therapy or prevention. In addition, compositions and treatment methods are provided for neutralizing microbial toxins, such as LPS, neutralizing proinflammatory cytokines, and for overcoming abnormalities of coagulation. The methods use appropriate antibody combinations and fusion proteins directed against different participating factors in the cascade leading to severe sepsis, septic shock, and various other immune-dysregulatory diseases.

In general, the dosage of administered antibodies will vary depending upon such factors as the patient's age, weight, height, sex, general medical condition and previous medical history. Typically, it is desirable to provide the recipient with a dosage of antibody component, immunoconjugate or fusion protein which is in the range of from about 1 pg/kg to 10 mg/kg (amount of agent/body weight of patient), although a lower or higher dosage also may be administered as circumstances dictate. These doses can be repeated as needed.

Administration of antibodies to a patient (human or domestic animal) can be intravenous, intraarterial, intraperitoneal, intramuscular, subcutaneous, intrapleural, intrathecal, by perfusion through a regional catheter, or by direct intralesional injection; it may also include inhalation, aerosols, or nasal application in certain diseases, such as asthma. When administering therapeutic proteins by injection, the administration may be by continuous infusion or by single or multiple boluses. Intravenous injection provides a useful mode of administration due to the thoroughness of the circulation in rapidly distributing antibodies.

Although unconjugated multispecific antibodies and antibody fragments and mixtures of unconjugated antibodies and antibody fragments are the preferred, primary therapeutic compositions for therapy according to the invention, the efficacy of such therapy can be enhanced by supplementing the multispecific antagonists with other therapies described herein. In such multimodal regimens, the supplemental therapeutic compositions can be administered before, concurrently or after administration of the multispecific antagonists. For example, multimodal therapy of Class M autoimmune diseases may comprise co-administration of therapeutics that are targeted against T-cells, plasma cells or macrophages, such as antibodies directed against T-cell epitopes, more particularly against the CD4 and CD5 epitopes. Gamma globulins also may be co-administered. In some cases, it may be desirable to co-administer immunosuppressive drugs such as corticosteroids and possibly also cytotoxic drugs. In this case, lower doses of the corticosteroids and cytotoxic drugs can be used as compared to the doses used in conventional therapies, thereby reducing the negative side effects of these therapeutics. When the disease to be treated is cancer, the use of various chemotherapeutic drugs, naked antibodies used in immunotherapy, and radiation (external or internal), can be combined with therapy according to the invention. Likewise, when infection and/or septicemia or septic shock are being treated, antimicrobial drugs may be used in combination with the multispecific antagonists.

In an alternative embodiment, the multispecific antagonists used for therapy are conjugated to a drug, toxin, enzyme, oligonucleotide, hormone, hormone antagonist, immunomodulator, boron compound or therapeutic radioisotope. Where the multispecific antagonist comprises a mixture of separate antibodies, only one of the antibodies may be conjugated, or more than one of the antibodies may be conjugated. In a further preferred embodiment, an antibody is used that comprises an arm that is specific for a low-molecular weight hapten to which a therapeutic agent is conjugated or fused. In this case, the antibody pretargets the B-cells, and the low-molecular weight hapten with the attached therapeutic agent is administered after the antibody has bound to the B-cell targets. Examples of recognizable haptens include, but are not limited to, chelators, such as DTPA and DOTA, fluorescein isothiocyanate, vitamin B-12 and other moieties to which specific antibodies can be raised, including also peptides and oligonucleotides. A preferred peptide is histamine-succinyl-glycine (HSG).

Therapeutically useful immunoconjugate can be obtained by conjugating a photoactive agent or dye to an antibody fusion protein. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, *Chem Britain* 22:430 (1986)). Moreover, monoclonal antibodies have been coupled with photoactivated dyes for achieving phototherapy. Mew et al., *J Immunol* 130:1473 (1983); idem., *Cancer Res* 45:4380 (1985); Oseroff et al., *Proc Natl Acad Sci USA* 83:8744 (1986); idem., *Photochem Photobiol* 46:83 (1987); Hasan et al., *Prog Clin Biol Res* 288:471 (1989); Tatsuta et al., *Lasers Surg Med* 9:422 (1989); Pelegrin et al., *Cancer* 67:2529 (1991). Thus, the present invention contemplates the therapeutic use of immunoconjugates comprising photoactive agents or dyes.

Drugs which are known to act on B-cells, plasma cells and/or T-cells are particularly useful in accordance with the present invention, whether conjugated to the multispecific antagonist, or administered as a separate component in combination with the multispecific antagonist. These include 5-fluorouracil, gemcitabine, methotrexate, doxorubicin, phenyl butyrate, bryostatin, cyclophosphamide, etoposide, bleomycin, doxorubicin, carmustine, vincristine, dacarbazine, procarbazine, taxol, platin derivatives, dexamethasone, leucovorin, prednisone, maytansinoids such as DM1, calicheamicin, rapamycin, leflunomide, FK506, immuran, fludarabine, azathioprine, mycophenolate, camptothecins (e.g., CPT-11, SN38), proteasome inhibitors (e.g., Velcade®), and cyclosporin. Drugs such as immuran, doxorubicin, methotrexate, and fludarabine which act on both B-cells and T-cells are particularly preferred. Illustrative of toxins which are suitably employed in accordance with the present invention are ricin, abrin, ribonuclease, DNase I, *Staphylococcus* enterotoxin-A, pokeweed antiviral protein, gelonin, diphtherin toxin, *Pseudomonas* exotoxin, *Pseudomonas* endotoxin and RNAses, such as onconase. See, for example, Pastan et al., *Cell* 47:641 (1986), and Goldenberg, Calif.—A Cancer Journal for Clinicians 44:43 (1994). Other suitable drugs and toxins are known to those of skill in the art.

Diagnostic Use of Multispecific Antagonists

Multispecific antagonists according to the invention also are useful in the diagnosis or detection of various conditions. In the context of this application, the terms "diagnosis" or "detection" can be used interchangeably. Whereas diagnosis usually refers to defining a tissue's specific histological status, detection recognizes and locates a tissue, lesion or organism containing a particular antigen. In these embodiments, the multispecific antagonists are conjugated to a diagnostic/detection agent. The construction and administration of diagnostic/detection agents is described in WO 04094613 and US Published Application no. 2004 0057902.

A diagnostic/detection agent is a molecule or atom, which may be administered conjugated to the multispecific antagonist and is useful in diagnosis or detection by binding to an antigen on cells that are localized at the site of a disease or condition according to the present invention. Useful diagnostic/detection agents include, but are not limited to, radioisotopes, dyes (such as with the biotin-streptavidin complex), radiopaque materials (e.g., iodine, barium, gallium, and thallium compounds and the like), contrast agents, fluorescent compounds or molecules and enhancing agents (e.g., paramagnetic ions) for magnetic resonance imaging (MRI), as well as for X-rays, ultrasound and computed tomography (CT).

Preferably, the diagnostic/detection agents are selected from the group consisting of radioisotopes for nuclear imaging, endoscopic and intravascular detection, enhancing agents for use in magnetic resonance imaging or in ultrasonography, radiopaque and contrast agents for X-rays and computed tomography, and fluorescent compounds for fluoroscopy, including endoscopic fluoroscopy. Fluorescent and radioactive agents conjugated to antibodies or used in bispecific, pretargeting methods, are particularly useful for endoscopic, intraoperative or intravascular detection of the targeted antigens associated with diseased tissues or clusters of cells, such as malignant tumors, as disclosed in Goldenberg U.S. Pat. Nos. 5,716,595 and 6,096,289, particularly with gamma-, beta-, and positron-emitters. Endoscopic applications may be used when there is spread to a structure that allows an endoscope, such as the colon, including orally-ingested cameras also used for imaging the gastrointestinal tract.

Multispecific antagonists according to the invention may comprise one or more radioactive isotopes useful for detecting diseased tissue. Particularly useful diagnostic radionuclides include, but are not limited to, $^{110}$In, $^{111}$In, $^{1777}$Lu, $^{18}$F, $^{52}$Fe, $^{62}$Cu, $^{64}$Cu, $^{67}$Cu, $^{67}$Ga, 68Ga, $^{86}$y, $^{90}$y, $^{89}$Zr, $^{94}$Tc, $^{94}$Tc, $^{99m}$Tc, $^{120}$I, $^{123}$I, $^{124}$I, $^{125}$I, $^{131}$I, $^{154\text{-}158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters, preferably with a decay energy in the range of 25 to 5,000 keV, more preferably in the range of 25 to 4,000 keV, and even more preferably in the range of 25 to 1,000 keV, and still more preferably in the range of 70 to 700 keV. Radionuclides useful for positron emission tomography include, but are not limited to: $^{18}$F, $^{52}$Mn, $^{52m}$Mn, $^{52}$Fe, $^{55}$Co, $^{62}$Cu, $^{61}$Cu, $^{68}$Ga, $^{72}$AS, $^{75}$Br, $^{76}$Br, $^{82m}$Rb, $^{83}$Sr, $^{86}$Y, $^{89}$Zr, $^{94m}$Tc, $^{110}$In, $^{120}$I, and $^{124}$I. Total decay energies of useful positron-emitting radionuclides are preferably <2,000 keV, more preferably under 1,000 keV, and most preferably <700 keV. Radionuclides useful as diagnostic/detection agents utilizing gamma-ray detection include, but are not limited to: $^{51}$Cr, $^{57}$Co, $^{58}$Co, $^{59}$Fe, $^{67}$Cu, $^{67}$Ga, $^{73}$Se, $^{97}$Ru, $^{99}$Tc, $^{111}$In, $^{114m}$I, $^{123}$I, $^{125}$I, $^{131}$I, $^{169}$Yb, $^{197}$Hg, and $^{201}$Tl. Decay energies of useful gamma-ray emitting radionuclides are preferably 20-2000 keV, more preferably 60-600 keV, and most preferably 100-300 keV. Radioisotopes may be bound to the multispecific antagonist either directly, or indirectly by using an intermediary functional group.

The method of diagnostic imaging with radiolabeled MAbs is well-known. In the technique of immunoscintigraphy, for example, antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY pp. 227-49, Pezzuto et al. (eds.) (Chapman & Hall 1993). The radiation dose delivered to the patient is maintained at as low a level as possible through the choice of isotope for the best combination of minimum half-life, minimum retention in the body, and minimum quantity of isotope which will permit detection and accurate measurement.

Metals are also useful in diagnostic/detection agents, including those for magnetic resonance imaging techniques. These metals include, but are not limited to: gadolinium, manganese, iron, chromium, copper, cobalt, nickel, dysprosium, rhenium, europium, terbium, holmium and neodymium. In order to load an antibody component with radioactive metals, paramagnetic ions, or other detectable moieties, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), tetraazacyclododecane-N,N',N",N'"-tetraacetic acid (DOTA), p-bromoacetamido-benzyl-tetraethylaminetetraacetic acid (TETA), or NOTA or other suitable peptide, porphyrins, polyamines, crown ethers, bisthiosemicarbazones, polyoximes, and like groups known to be useful for this purpose. Chelates are coupled to the antibodies using standard chemistries. The chelate is normally linked to the antibody by a group, which enables formation of a bond to the molecule with minimal loss of immunoreactivity and minimal aggregation and/or internal cross-linking. Other, more unusual, methods and reagents for conjugating chelates to antibodies are disclosed in U.S. Pat. No. 4,824,659 to Hawthorne, entitled "Antibody Conjugates," issued Apr. 25, 1989.

Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$n, $^{67}$Ga, $^{68}$Ga, $^{99m}$Tc, $^{94m}$Tc, $^{11}$C, $^{13}$N, $^{15}$O, $^{76}$Br, for radio-imaging. The same chelates, when complexed with non-radioactive metals, such as manganese, iron and gadolinium are useful for MRI, when used along with the antibodies of the invention. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed by the invention.

Contrast agents include enhancing agents for use in magnetic resonance imaging, as well as CT contrast agents, and ultrasound contrast agents. Paramagnetic ions suitable in detection and diagnosis according to the present invention include chromium (III), manganese (II), iron (III), iron (II), cobalt (II), nickel (II), copper (H), neodymium (III), samarium (III), ytterbium (III), gadolinium (III), vanadium (II), terbium (III), dysprosium (III), holmium (III) and erbium (III. Preferred magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention, with gadolinium being particularly preferred. U.S. Pat. No. 6,331,175 describes MRI technique and the preparation of antibodies conjugated to an MRI enhancing agent. Preferred ultrasound contrast agents may comprise more than one image-enhancing agent for use in ultrasound imaging. In a preferred embodiment, the contrast agent is a liposome. Preferably, the liposome comprises a bivalent DTPA-peptide covalently attached to the outside surface of the liposome. Preferably the liposome is gas filled.

Ions useful in other contexts, such as X-ray imaging, include but are not limited to lanthanum (III), gold (III), lead (II), and especially bismuth (III). Fluorescent labels include rhodamine, fluorescein and renographin. Rhodamine and fluorescein are often linked via an isothiocyanate intermediate.

Radiopaque and contrast materials are used for enhancing X-rays and computed tomography, and include iodine compounds, barium compounds, gallium compounds, thallium compounds, etc. Specific compounds include barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

The multispecific antagonists of the present invention also can be labeled with a fluorescent compound. The presence of a fluorescent-labeled MAb is determined by exposing the antibody to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

As in therapeutic modalities, administration of multispecific antagonists for diagnosis can be effected in a mammal by intravenous, intraarterial, intraperitoneal, intramuscular, subcutaneous, intrapleural, intrathecal, perfusion through a regional catheter, or direct intralesional injection. When administering the antibody by injection, the administration may be by continuous infusion or by single or multiple boluses. Diagnosis further requires the step of detecting the bound proteins with known techniques. A single multispecific antagonist can be used for both therapy and diagnosis/detection at the same time.

For purposes of diagnosis and detection, the multispecific antagonists are administered to a patient in a diagnostically effective amount in a pharmaceutically acceptable carrier. In this regard, a "diagnostically effective amount" is one that is capable of being detected by the equipment associated with detection once the antagonist has localized and excess antagonist has cleared from the bloodstream.

The present invention, thus generally described, will be understood more readily by reference to the following examples, which are provided by way of illustration and are not intended to be limiting of the present invention. The examples demonstrate that multispecific antagonists according to the invention prevent septic shock in animal models and improve signs and symptoms in patients with cancer-related cachexia, autoimmune disease and atherosclerotic plaques.

EXAMPLE 1

Treatment of Septic Shock

JR is a 72-year-old white male with a history of non-Hodgkin's lymphoma having past therapy with various cytotoxic drugs, corticosteroids, as well as Rituxan®, and presenting with stable lymphoma and a past history of several infections that required prolonged antibiotic therapy. He is admitted to the emergency department after being evaluated by his general practitioner with high temperature (40.7° C.), chills, dyspnea, palpitations, agitation, some confusion, and cool extremities. Examination reveals tachycardia (>90/min), hypotension (95/60 mm Hg), especially upon standing, and a reduced urine output (800 mL/d), and signs of pneumonia Tests show a low oxygen tension and acidosis, a blood count not detecting infection, but instead neurtopenia (3,500 WBC/mL, with 10% bands), platelets of 48,000, Hg of 6 g/dL, chest x-ray reveals a generalized pneumonia, blood tests indicate reduced renal function, with abnormal serum creatinine (3 mg/dL) and BUN levels, and elevated serum lactate indicates tissue hypoperfusion. Blood cultures reveal the presence of *S. aureus* and Gram-negative bacteria, supporting the diagnosis of septicemia. The patient is treated in the intensive care unit for severe sepsis and septic shock, which includes general supportive care (oxygen), hemodynamic support by fluid infusion to restore circulating blood volume (500 mL 0.9% sodium chloride and lactated Ringer solution, with up to 2 L given over first few hours), vasopressor supportive therapy with dopamine (Intropin, 3 mcg/kg/min iv), and antibiotic therapy with 400 mg IV every 12 hrs of ciprofloxacin (Cipro). The patient is also given drotecogin alfa (activated protein C) at 24 microg/kg/hr for a total of 96 hrs. Five days after admission, the patient is stable but does not show any significant improvement in signs or symptoms, only slightly better urine excretion, a small rise in blood pressure, and a small drop in temperature to 39.3° C. The patient is then given a combination of two humanized monoclonal antibodies sequentially twice weekly for 3 weeks, consisting of 300 mg anti-MIF and 400 mg anti-LPS antibody, both by slow infusions over 4 hrs. During the second week, the patient shows less confusion, a further drop in temperature, reduction of tachycardia, dyspnea, and reduced pneumonia by both physical exam and chest x-ray. At the end of the 3$^{rd}$ week, his renal function tests also show some improvement (BUN and serum creatinine values), and he is removed from the intensive care unit to an infectious disease bed, with supportive care adjusted. Two months later, the patient receives a repeated cycle of activated protein C and the anti-MIF and anti-LPS antibodies, as well as a repeated course of broad-spectrum antibiotic, and then shows further improvement so that he becomes ambulatory and has virtually normal mental function and an overall 80+% reduction of pneumonia and a fever of 38.5° C., and about an 80% normal urine output.

EXAMPLE 2

Therapy of Systemic Lupus Erythematosus (SLE)

S. R is a 32-year-old African-American female diagnosed 5 years earlier with SLE, when she presented with a globerulonephritis (WHO grade 3), serositis, polyarthritis, and a vasculitic rash. She had prior therapy with corticosteroids (range of 15-60 mg per day) and hydroxychloroquine (200 mg/day), and at a later time also azathioprine (100 mg/day) and a course of cyclophosphamide) because of persistent disease. Over the years, she experienced flares of her SLE, presenting with polyarthritis, lethargy, skin rash, and serositis. She now presents with persistently active disease and unresponsive to conventional therapies, but is maintained on 40 mg prednisone daily. She is given humanized anti-CD22 monoclonal antibody, epratuzumab, at 400 mg i.v. over 1 hr, repeated once in each of the following two weeks. Four weeks after the third infusion, her circulating B-lymphocytes are reduced by 40% from baseline prior to therapy, but her Hg level has risen from 8 g/dL to 10 g/dL. Her rash and polyarthritis show some improvement, yet she requires additional therapy. At 8 weeks following her anti-CD22 antibody therapy, she is given a course of a bispecific antibody fusion protein consisting of a recombinant heteroconjugate of an anti-CD83 and an anti-TNF-α antibody, at a dose of 500 mg i.v. weekly×4 weeks. At evaluation at 2 months later, she has a marked improvement in all organ systems, to a BILAG C and D status in most, and is capable of having her prednisone dose tapered to 7.5 mg per day. At follow-up of 3 months, most of her organ symptoms remain stable, and she remains on this low does of prednisone without any flare.

EXAMPLE 3

Therapy of Non-Hodgkin's Lymphoma (NHL)

SL is a 66-year-old white male with a history of diffuse large-cell NHL that has relapsed after therapy with CHOP and rituximab, and is now presenting with fever, lung and mediastinal infiltrates, enlarged cervical and axillary lymph nodes, and evidence of bone marrow involvement based on aspiration and cytology. He receives 6 weekly infusions of two humanized antibodies, one against TNF-α and the other against MIF, each given on the same day sequentially, over a 34-hr infusion for each, at a dose of each of 450 mg. Twenty-four hours after the last infusion, his examination indicates that he has no major toxicities to the therapy, and some palpable softening of his cervical and axillary lymph nodes. At the next follow-up examination in 8 weeks, almost all of his cervical and about half of these axillary nodes have disappeared, and his chest x-ray and CT scan show evidence of about a 60% shrinkage of his pulmonary and mediastinal infiltrates. About 4 months later, his examination reveals that although his lymph node and pulmonary involvement are stable, there is a suggested increase in bone marrow involvement and a drop in his Hg to 8 g/dL. He then receives a bispecific antibody consisting of a fused humanized antibody against MIF and against IL-6, given twice weekly for 3 weeks at a dose of 500 mg per slow i.v. infusion. At his 3-month evaluation, his Hg shows a rise to 11 g/dL, there is a remarkable decrease of NHL cells in the bone marrow aspirate, and there are no lymph nodes palpable or disease visible in the chest by radiological examinations. The patient's response remains stable for another 6 months.

Example 4

Therapy of Cancer-related Cachexia

NR is a 58-year-old African-American male with a history of heavy cigarette smoking and an inoperable non-small-cell lung cancer affecting his left lung and paraortic and parabronchial lymph nodes on both sides. He has received combination chemotherapy, which has shown myelotoxicities and evidence of some minor tumor shrinkage, being less than 40% of all measurable volume. He presents with considerable weight loss, being almost 2 meters high and now weighing 68 kg, suffering from cancer-related cachexia. He is infused weekly for 8 weeks with a humanized bispecific fusion antibody construct targeting both IL-6 and TNF-α, at a dose of 600 mg weekly. During the last 3 weeks, his appetite improves and he shows a weight gain to 75 kg at 7 weeks post therapy, with more muscle strength and generally improved vigor, which then remains stable at 75-80 kg over the next 2 months, when he begins to show progression of his malignant disease. Other than his cyclic chemotherapy, no corticosteroids were given during the antibody therapy, and he is considered to have responded to this treatment for cachexia.

EXAMPLE 5

Therapy of Renal Cell Carcinoma

JR is a 45-year-old white female presenting with a mass on her left kidney and involvement of her paraortic lymph nodes on the left side and a 3×4 cm focus of disease in her upper left lung. She undergoes complete resection of her left kidney, with evacuation of adjacent lymph nodes. Six weeks later, she is given 7 weekly i.v. infusions of humanized IL-6 antibody fused with IL-2 cytokine, at a dose of 500 mg (antibody protein), which is repeated 4 months later. At her follow-up examination 3 months following the last therapy, her examination reveals a 60% reduction of her lung metastasis, and no evidence of new disease elsewhere.

EXAMPLE 6

Therapy of Rectal Carcinoma

PS is a 70-year-old white female with a history of total mesorectal extirpation of a rectal adenocarcinoma (T3N2) and adjuvant chemoradiation (continuous infusion 5-fluorouracil and fractionated, 1.8-Gy doses, five days per week over a period of 5 and a half weeks, total dose of 45 Gy external beam radiation). She does not have post surgical chemotherapy, and 6 months later presents with 3 metastases in the lower right lobe of the liver, ranging from 2 to 4 cm in diameter, and a serum CEA titer of 16.4 ng/mL. The primary rectal cancer is evaluated by immunohistochemistry and shows a high expression of both CD59 and CEACAM6. She then receives 350 mg of a bispecific antibody consisting of a recombinantly fused humanized anti-CD59 antibody and humanized anti-CEACAM6 antibody, given once weekly for 8 weeks, alongside a continuous infusion of fluorouracil for a period of 5 weeks. At follow-up 2 months post the last antibody infusion, the patient's blood CEA titer drops to 12 ng/mL, but with no change by CT scans in the size of the liver metastases. After an additional 3 months, the blood CEA is 7 ng/mL, and there is disappearance by CT scanning of the smallest liver metastasis and shrinkage by about 50% of the other two. The disease remains stable for another 2 months, at which time the blood CEA level rises to 10 ng/mL, but no change yet in the size of the liver metastases.

Thus, methods and compositions for immunotherapy of inflammatory and immune-dysregulatory diseases and cancers according to the present invention have been described. Many modifications and variations may be made to the techniques and structures described and illustrated herein without departing from the spirit and scope of the invention. Accordingly, it should be understood that the compositions and methods described herein are illustrative only and are not limiting upon the scope of the invention.

The contents of all documents, references and citations referenced above, including their references, are incorporated herein in their entirety.

The invention claimed is:

1. A bispecific antibody that binds with two different targets, wherein said targets are selected from (i) a complement regulatory protein and (ii) a target associated with septicemia, sepsis or septic shock selected from the group consisting of LPS, HMGB-1, MIF, TNFα, TF, VEGF, and IL-6, wherein said bispecific antibody is an immunoconjugate that comprises a diagnostic/detection agent or a therapeutic agent.

2. A bispecific antibody according to claim 1, wherein one arm of said antibody reacts specifically with a complement regulatory protein.

3. A bispecific antibody according to claim 1, additionally comprising a secondary therapeutic which (i) is a cytokine or a chemokine, (ii) affects coagulation or (iii) affects T cells or B-cells.

4. A bispecific antibody according to claim 3, additionally comprising a secondary therapeutic that affects coagulation.

5. A bispecific antibody according to claim 3, additionally comprising a secondary therapeutic that affects T cells or B cells.

6. A bispecific antibody according to claim 3, additionally comprising a cytokine or chemokine.

7. A bispecific antibody according to claim 1, wherein said bispecific antibody is an immunoconjugate that comprises a therapeutic agent.

8. A bispecific antibody according to claim 1, wherein (ii) is a target selected from the group consisting of HMGB-1, MIF, and TF.

9. A bispecific antibody according to claim 1, wherein said bispecific antibody reacts with MIF and a complement regulatory protein selected from the group consisting of CD46, CD55, CD59, and mCRP.

10. A bispecific antibody according to claim 1, wherein said bispecific antibody reacts with HMGB-1 and a complement regulatory protein selected from the group consisting of CD46, CD55, CD59, and mCRP.

11. A bispecific antibody according to claim 1, wherein said bispecific antibody reacts with LPS and a complement regulatory protein selected from the group consisting of CD46, CD55, CD59, and mCRP.

12. A bispecific antibody according to claim 1, wherein said bispecific antibody reacts with TF and a complement regulatory protein selected from the group consisting of CD46, CD55, CD59, and mCRP.

13. A bispecific antibody according to claim 1, wherein said bispecific antibody reacts with TNFα and a complement regulatory protein selected from the group consisting of CD46, CD55, CD59, and mCRP.

\* \* \* \* \*